(12) United States Patent
Rothemund

(10) Patent No.: US 7,842,793 B2
(45) Date of Patent: Nov. 30, 2010

(54) METHODS OF MAKING NUCLEIC ACID NANOSTRUCTURES

(75) Inventor: Paul W. K. Rothemund, Pasadena, CA (US)

(73) Assignee: The California Institute of Technology, Pasadena, CA (US)

( * ) Notice: Subject to any disclaimer, the term of this patent is extended or adjusted under 35 U.S.C. 154(b) by 191 days.

(21) Appl. No.: 11/452,699

(22) Filed: Jun. 14, 2006

(65) Prior Publication Data

US 2007/0117109 A1 May 24, 2007

Related U.S. Application Data

(60) Provisional application No. 60/690,533, filed on Jun. 14, 2005.

(51) Int. Cl.
*C07H 21/04* (2006.01)
(52) U.S. Cl. .............. 536/23.1; 536/24.1; 977/704; 977/707; 977/711; 977/724; 977/728
(58) Field of Classification Search .............. None
See application file for complete search history.

(56) References Cited

U.S. PATENT DOCUMENTS 6,255,469 B1 * 7/2001 Seeman et al. ............. 536/23.1
2005/0136453 A1 6/2005 Sherman et al.
2006/0078910 A1 4/2006 Seeman et al.
2009/0018028 A1 * 1/2009 Lindsay et al. ............. 506/9

OTHER PUBLICATIONS

Lewin, B. Genes V, Oxford University Press, Oxford, 1994, p. 120.*
Barish, Robert D., "Two computational Primitives for Algorithmic Self-Assembly: Copying and Counting" *Nanoletters* 2005.
Chen, Junghuei and Seeman, Nadrian C., "Synthesis from DNA of a molecule with the connectivity of a cube" *Nature*, Apr. 1991. pp. 631-633, vol. 350, Nature Publishing Group.
Chworos, Arkadiusz et al., "Buillding Programmable Jigsaw Puzzles with RNA" *Science* Dec. 2004. pp. 2068-2072, vol. 306.
Cuberes, M.T, et al., "Room-temperature repositioning of individual $C_{60}$ molecules at Cu steps: Operation of a molecular counting device" *Appl. Phys. Lett*, Nov. 1996. pp. 3016-3018, vol. 69.
Eigler, D.M, et al., "Positioning single atoms with a scanning tunnelling microscope" *Nature* Apr. 1990., pp. 524-526, vol. 344.
Feynman, Richard P. "Plenty of Room at the Bottom" Dec. 1959 California Institute of Technology.
Fu, Tsu-Ju, et al., "DNA Double Crossover Molecules" *Biochemistry*. 1993. pp. 3211-3220. vol. 32. American Chemical Society.

(Continued)

*Primary Examiner*—BJ Forman
(74) *Attorney, Agent, or Firm*—Joseph R. Baker, Jr.; Gavrilovich, Dodd & Lindsey, LLP

(57) ABSTRACT

The disclosure relates to methods and composition for generating nanoscale devices, systems, and enzyme factories based upon a nucleic acid nanostructure the can be designed to have a predetermined structure.

39 Claims, 12 Drawing Sheets

OTHER PUBLICATIONS

Gothelf, Kurt, et al., "DNA—programmed assembly of nanostructures" *Org. Biomol. Chem.* 2005. pp. 4023-4037. vol. 3 The Royal Society of Chemistry.

Heinrich, A. J., et al., "Molecule Cascades" *Science* Nov. 2002. pp. 1381-1387.

Junno, T., et al., "Controlled manipulation of nanoparticles with an atomic force microscope" *Appl. Phys. Lett.* Jun. 1995. pp. 3627-3629. vol. 66.

Labean, Thomas, et al., "Experimental Progress in Computation by Self-Assembly of DNA things" *DIMACS Series in Discrete Mathematics and Theoretical Computer Science*.

Labean, Thomas, "Introduction to Self-Assembly DNA Nanostructures for Computation and Nanofabrication" pp. 35-58.

Labean, Thomas, et al., "Overview of New Structures for DNA-based Nanofabrication and Computation" *Computer Science*, Duke University.

Le, John D., et al., "DNA-Tempered Self-Assemby of Metallic Nanocomponent Arrays on a Surface" *Nanoletters*. 2004. pp. 2343-2347. vol. 4, No. 12. American Chemical Society.

Mao, Chengde, et al., "Designed Two-Dimensional DNA Holiday Junction Arrays Visualized by Atomic Force Microscopy" *J. Am. Chem. Soc.* 1999. pp. 5437-5443. vol. 121. American Chemical Society.

Mao, Chuanbin, et al., "Virus-Based Toolkit for the Directed Synthesis of Magnetic and Semiconducting Nanowires" *Science* Jan. 2002. pp. 213-217. vol. 303.

Park Sung Ha, et al., "Finite-Size, Fully Addressable DNA Tile Lattices Formed by Hierarchical Assemby Procedures" *Agnew. Chem. Int. Ed.* 2006. pp. 735-739. vol. 45.

Park, Sung Ha, "Three Helix Bundle DNA Tiles Self-Assemble into 2D Lattice of 1D Templates for Silver Nanowires" *Nanoletters*. 2005. pp. 693-696. vol. 5, No. 4. American Chemical Society.

Park, Sung Ha, "Electronic nanostructures templated on self-assembly DNA scaffolds" *Nanotechnology*.2004. pp. S525-S527. vol. 15. Institute of Physics Publishing.

Reif, John H., "Molecular Assembly and Computation: From Theory to Experimental Demonstrations".

Rothemund, Paul W.K., et al., "Algorithmic Self-Assembly of DNA Sierpinski Triangles" *PLOS Biology*. Dec. 2004. pp. 2041-2053. vol. 2, Issue 12.

Rothemund, Paul W.K., et al., "Design and Characterization of Programmable DNA Nanotubes" *J. Am. Chem Soc.* 2004, pp. 16344-16352. vol. 126.

Rothemund, Paul W.K., "Design of DNA origami" *Proceedings of the Intl. Conference of Computer-Aided Design (ICCAD)* 2005.

Rothemund, Paul W.K., "Folding DNA to create nanoscale shapes and patterns" *Nature* Mar. 2006. pp. 297-302. vol. 440.

Rothemund, Paul W.K., "Generation of arbitrary nanoscale shapes and patterns by scaffolded DNA origami Supplementary Material".

Rothemund, Paul W.K. "Scaffolded DNA origami; from generalized multi-crossovers to polygonal networks".

Schulman, Rebecca, "Self-Replication and Evolution of DNA Crystals" California Institute of Technology.

Seeman, Nadrian C., De Novo Design of Sequences for Nucleic Acid Structural Engineering. *Journal of Biomolecular Structure & Dynamics* 1990. pp. 573-581. vol. 8, Issue No. 3. Adenine Press.

Seeman, Nadrian C., "Nucleic Acid Junctions and Lattices" *J. Theor. Biol.*, 1982. pp. 237-247. Academic Press Inc.

Seeman, Nadrian C., "Nucelic acid nanostructures: bottom-up control of geometry on the nanoscale" *Rep. Prog. Phys* 2005. pp. 237-270. vol. 68. Institute of Physics Publishing.

Shih, William M., et al., "A 1.7-kilobase single-stranded DNA that folds into a nanoscale octahedron" *Nature* Feb. 2004. pp. 618-621. vol. 427.

Soloveichik, David and Erik Winfree. "Complexity of Compact Proofreading for Self-Assembled Patterns" Department of CNS and CS,California Institute of Technology.

Valentine, James W. et al., "Morphological complexity increase in metazoans" *Paleobiology* 199. pp. 131-142. vol. 20 (2). The Paleontological Society.

Whitesides, George M., "Molecular Self-Assembly and Nanochemistry A chemical strategy for the synthesis of nanostructures" *Science* Nov. 1991 pp. 1312-1319. vol. 254.

Winfree, Erik, et al., "Design and self-assembly of two-dimensional DNA Crystals" *Nature*. Aug. 1998. pp. 539-544. vol. 394 Macmillian Publishers.

Winfree, Erik "On the computational power of DNA Annealing and Litigation" California Institute of Technology.

Winfree, Erik. "Self-Healing Tile Sets" California Institute of Technology.

Yan, Hao, et al., "Directed nucleation assembly of DNA tile complexes for barcode-patterned lattices" *PNAS* Jul. 2003. pp. 8103-8108. vol. 100, No. 14.

Yan, Hao, et al., "DNA-Templated Self-Assembly of Protein Arrays and Highly Conductive Nanowires" *Science*. Sep. 2003. pp. 1882-1884. vol. 301.

Yokoyama, Takashi, et al., "Selective assembly on a surface of supramolecular aggregates with controlled sizes and shape" *Nature* Oct. 2003. pp. 619-621. vol. 413.

Zhang, Yuwen, "Construction of a DNA-Truncated Octahedron" *J. Am. Chem Soc.* 1994. pp. 1661-1669. vol. 116. American Chemical Society.

Zinder, Norton D., "Multiregulatory element of filamentous bacteriophages" *Microbiological Reviews*. Jun. 1985. pp. 101-106. American Society for Microbiology.

\* cited by examiner

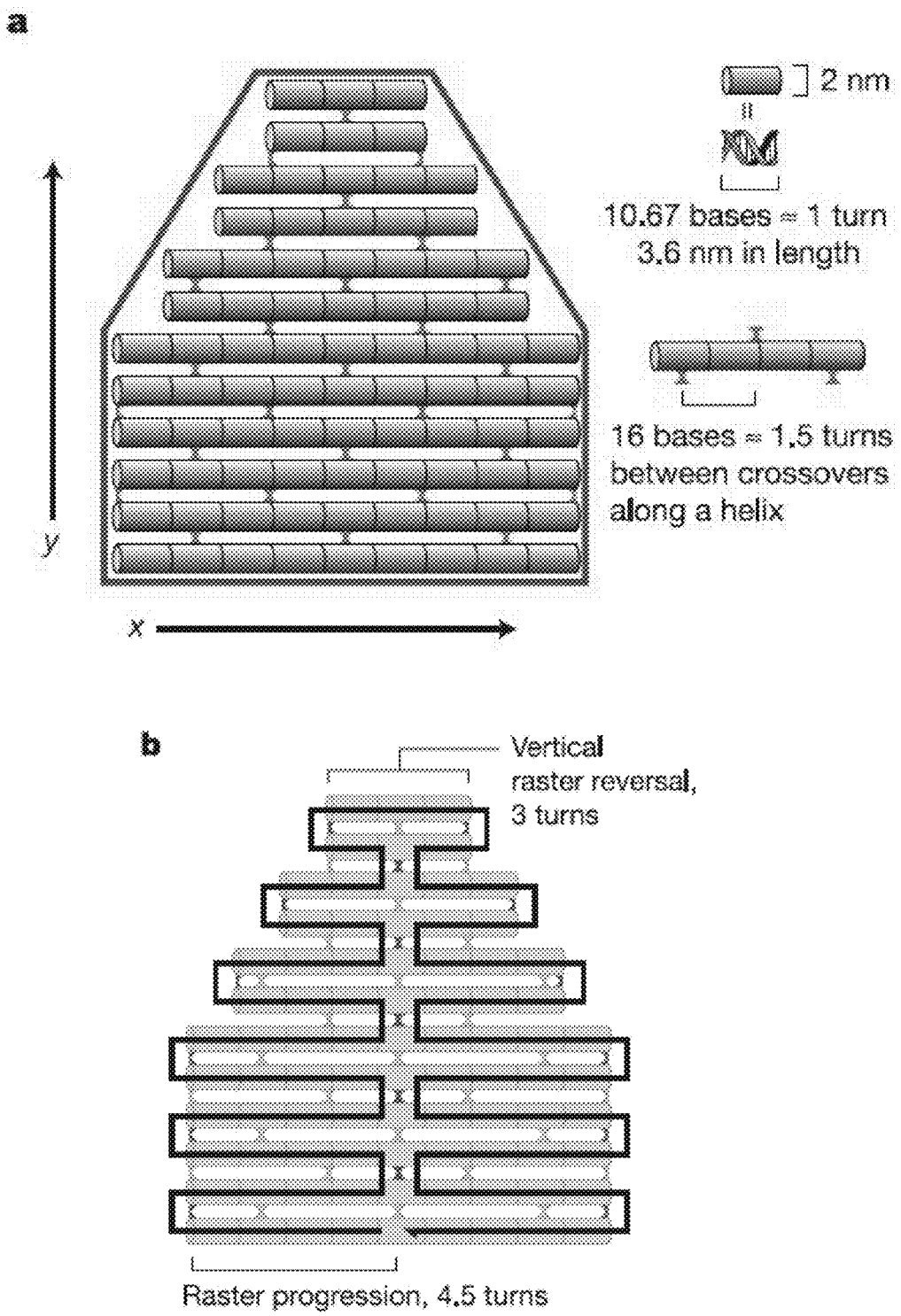
FIGURE 2A-B

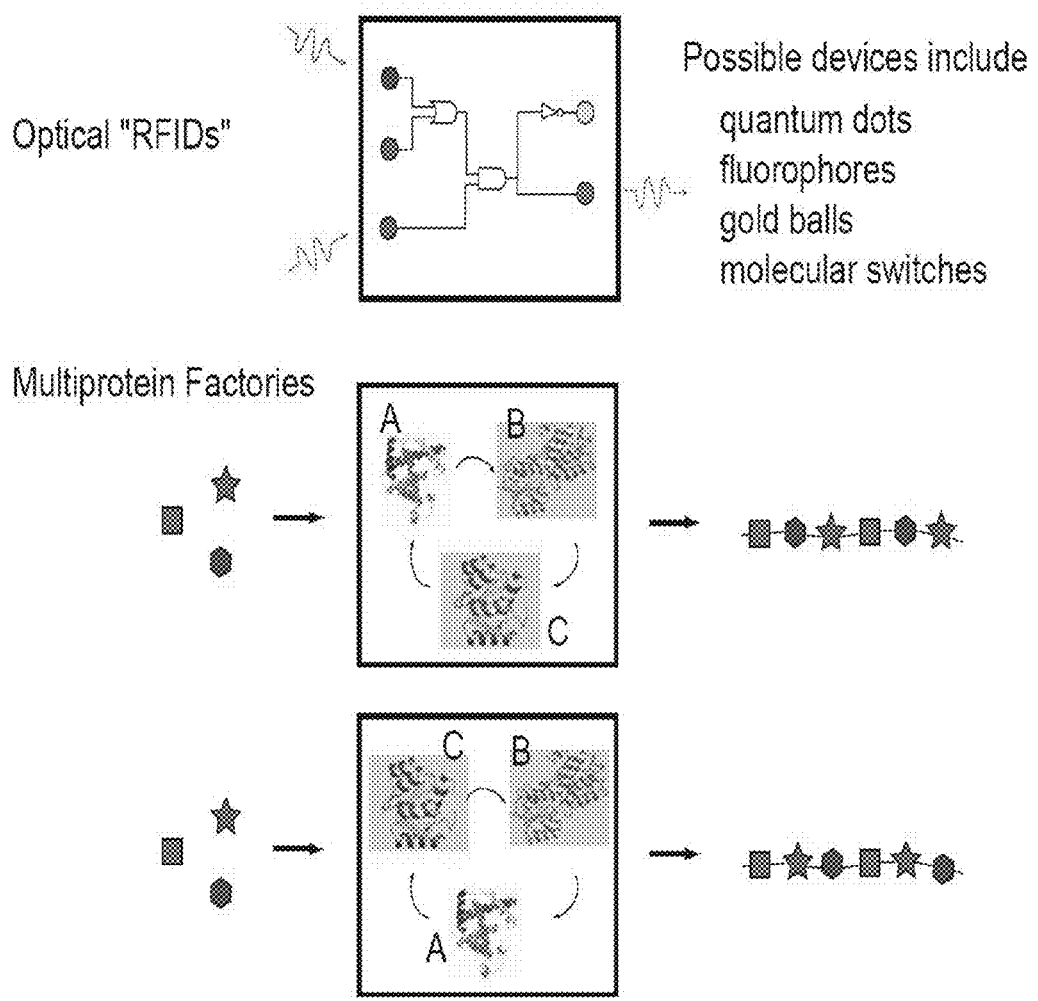
FIGURE 7A-B

SEQUENCE LISTING

<160> NUMBER OF SEQ ID NOS: 24

<210> SEQ ID NO 1
<211> LENGTH: 7249
<212> TYPE: DNA
<213> ORGANISM: Artificial Sequence
<220> FEATURE:
<223> OTHER INFORMATION: m13mp18 Cloning Vector

<400> SEQUENCE: 1

```
aatgctacta ctattagtag aattgatgcc accttttcag ctcgcgcccc aaatgaaaat    60
atagctaaac aggttattga ccatttgcga aatgtatcta atggtcaaac taaatctact   120
cgttcgcaga attgggaatc aactgttaca tggaatgaaa cttccagaca ccgtacttta   180
gttgcatatt taaaacatgt tgagctacag caccagattc agcaattaag ctctaagcca   240
tccgcaaaaa tgacctctta tcaaaaggag caattaaagg tactctctaa tcctgacctg   300
ttggagtttg cttccggtct ggttcgcttt gaagctcgaa ttaaaacgcg atatttgaag   360
tctttcgggc ttcctcttaa tcttttgat gcaatccgct ttgcttctga ctataatagt    420
cagggtaaag acctgatttt tgatttatgg tcattctcgt tttctgaact gtttaaagca   480 tttgagggg attcaatgaa tatttatgac gattccgcag tattggacgc tatccagtct    540
aaacatttta ctattacccc ctctggcaaa acttcttttg caaaagcctc tcgctatttt   600 ggttttatc gtcgtctggt aaacgagggt tatgatagtg ttgctcttac tatgcctcgt    660
aattcctttt ggcgttatgt atctgcatta gttgaatgtg gtattcctaa atctcaactg   720
atgaatcttt ctacctgtaa taatgttgtt ccgttagttc gttttattaa cgtagatttt   780
tcttcccaac gtcctgactg gtataatgag ccagttctta aaatcgcata aggtaattca   840
caatgattaa agttgaaatt aaaccatctc aagcccaatt tactactcgt tctggtgttc   900
tcgtcagggc aagccttatt cactgaatga gcagctttgt tacgttgatt tgggtaatga   960
atatccggtt cttgtcaaga ttactcttga tgaaggtcag ccagcctatg cgcctggtct  1020
gtacaccgtt catctgtcct cttcaaagt tggtcagttc ggttccctta tgattgaccg    1080
tctgcgcctc gttccggcta agtaacatgg agcaggtcgc ggatttcgac acaatttatc   1140
aggcgatgat acaaatctcc gttgtacttt gtttcgcgct tggtataatc gctggggtc    1200 aaagatgagt gttttagtgt attctttcgc ctctttcgtt ttaggttggt gccttcgtag   1260
tggcattacg tattttaccc gtttaatgga aacttcctca tgaaaaagtc tttagtcctc   1320
aaagcctctg tagccgttgc taccctcgtt ccgatgctgt ctttcgctgc tgagggtgac   1380
gatcccgcaa aagcggcctt taactccctg caagcctcag cgaccgaata tatcggttat   1440
gcgtgggcga tggttgttgt cattgtcggc gcaactatcg gtatcaagct gtttaagaaa   1500
ttcacctcga aagcaagctg ataaaccgat acaattaaag ctccttttg gagcctttt    1560 ttttggagat tttcaacgtg aaaaaattat tattcgcaat cctttagtt gttcctttct    1620 attctcactc cgctgaaact gttgaaagtt gtttagcaaa accccataca gaaaattcat   1680
ttactaacgt ctggaaagac gacaaaactt tagatcgtta cgctaactat gagggttgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
ctgagggtgg cggttctgag ggtggcggta ctaaacctcc tgagtacggt gatacaccta   1920
ttccgggcta cttatatc aaccctctcg acggcactta tccgcctggt actgagcaaa     1980
accccgctaa tcctaatcct tctcttgagg agtctcagcc tcttaatact ttcatgtttc   2040
agaataatag gttccgaaat aggcaggggg cattaactgt ttatacgggc actgttactc   2100
aaggcactga ccccgttaaa acttattacc agtacactcc tgtatcatca aaagccatgt   2160
atgacgctta ctggaacggt aaattcagag actgcgcttt ccattctggc tttaatgaag   2220
atccattcgt ttgtgaatat caaggccaat cgtctgacct gcctcaacct cctgtcaatg   2280
ctggcggcgg ctctggtggt ggttctggtg cggctctga gggtggtggc tctgagggtg    2340
gcggttctga gggtggcggc tctgagggag gcggttccgg tggtggctct ggttccggtg   2400
```

```
attttgatta tgaaaagatg gcaaacgcta ataaggggc tatgaccgaa aatgccgatg    2460
aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttag cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt ccttctggt aactttgttc ggctatctgc ttacttttct    2940 taaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttga cgttaaacaa aaaatcgttt ctttatttgga    3180 ttgggataaa taatatggct gttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttttctagt aattatgatt    3840 ccggtgttta ttcttattta acgccttatt tatcacacgg tcggtatttc aaaccattaa    3900
atttaggtca gaagatgaaa ttaactaaaa tatatttgaa aaagtttct cgcgttcttt    3960 gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200 ttaaaaagg taattcaaat gaaattgtta aatgtaatta attttgtttt cttgatgttt    4260
gtttcatcat cttctttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg ctaataattt tgatatggtt ggttcaattc cttccataat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
```

```
agtgcaccta aagatatttt agataaccct cctcaattcc tttctactgt tgatttgcca   4800
actgaccaga tattgattga gggtttgata tttgaggttc agcaaggtga tgctttagat   4860
ttttcatttg ctgctggctc tcagcgtggc actgttgcag gcggtgttaa tactgaccgc   4920
ctcacctctg ttttatcttc tgctggtggt tcgttcggta tttttaatgg cgatgtttta   4980
gggctatcag ttcgcgcatt aaagactaat agccattcaa aatattgtc tgtgccacgt    5040
attcttacgc tttcaggtca aagggttct atctctgttg ccagaatgt cccttttatt     5100
actggtcgtg tgactggtga atctgccaat gtaaataatc catttcagac gattgagcgt   5160
caaaatgtag gtatttccat gagcgttttt cctgttgcaa tggctggcgg taatattgtt   5220
ctggatatta ccagcaaggc cgatagtttg agttcttcta ctcaggcaag tgatgttatt   5280
actaatcaaa gaagtattgc tacaacggtt aatttgcgtg atggacagac tcttttactc   5340
ggtggcctca ctgattataa aaacacttct caagattctg gcgtaccgtt cctgtctaaa   5400
atcccttttaa tcggcctcct gtttagctcc cgctctgatt ccaacgagga aagcacgtta   5460
tacgtgctcg tcaaagcaac catagtacgc gccctgtagc ggcgcattaa gcgcggcggg   5520
tgtggtggtt acgcgcagcg tgaccgctac acttgccagc gccctagcgc ccgctccttt   5580
cgctttcttc ccttcctttc tcgccacgtt cgccggcttt ccccgtcaag ctctaaatcg   5640
ggggctccct ttagggttcc gatttagtgc tttacggcac ctcgaccca aaaaacttga    5700
tttgggtgat ggttcacgta gtgggccatc gccctgatag acggtttttc gccctttgac   5760
gttgagtcc acgttcttta atagtggact cttgttccaa actggaacaa cactcaaccc    5820
tatctcgggc tattcttttg atttataagg gattttgccg atttcggaac caccatcaaa   5880
caggattttc gcctgctggg gcaaaccagc gtggaccgct tgctgcaact ctctcagggc   5940
caggcggtga agggcaatca gctgttgccc gtctcgctgg tgaaaagaaa aaccaccctg   6000
gcgcccaata cgcaaaccgc ctctccccgc gcgttggccg attcattaat gcagctggca   6060
cgacaggttt cccgactgga aagcgggcag tgagcgcaac gcaattaatg tgagttagct   6120
cactcattag gcaccccagg ctttacactt tatgcttccg gctcgtatgt tgtgtggaat   6180
tgtgagcgga taacaatttc acacaggaaa cagctatgac catgattacg aattcgagct   6240
cggtacccgg ggatcctcta gagtcgacct gcaggcatgc aagcttggca ctggccgtcg   6300
ttttacaacg tcgtgactgg gaaaaccctg gcgttaccca acttaatcgc cttgcagcac   6360
atccccttt cgccagctgg cgtaatagcg aagaggcccg caccgatcgc ccttcccaac    6420
agttgcgcag cctgaatggc gaatggcgct ttgcctggtt tccggcacca gaagcggtgc   6480
cggaaagctg gctggagtgc gatcttcctg aggccgatac ggtcgtcgtc ccctcaaact   6540
ggcagatgca cggttacgat gcgcccatct acaccaacgt aacctatccc attacggtca   6600
atccgccgtt tgttcccacg gagaatccga cgggttgtta ctcgctcaca tttaatgttg   6660
atgaaagctg gctacaggaa ggccagacgc gaattatttt tgatggcgtt cctattggtt   6720
aaaaaatgag ctgatttaac aaaaatttaa cgcgaatttt aacaaaatat taacgtttac   6780
aatttaaata tttgcttata caatcttcct gttttggggg cttttctgat tatcaaccgg   6840
ggtacatatg attgacatgc tagttttacg attaccgttc atcgattctc ttgtttgctc   6900
cagactctca ggcaatgacc tgatagcctt tgtagatctc tcaaaaatag ctaccctctc   6960
cggcattaat ttatcagcta gaacggttga atatcatatt gatggtgatt tgactgtctc   7020
cggccttttct caccctttg aatctttacc tacacattac tcaggcattg catttaaaat   7080
atatgagggt tctaaaaatt tttatccttg cgttgaaata aaggcttctc ccgcaaaagt   7140
```

```
attacagggt cataatgttt ttggtacaac cgatttagct ttatgctctg aggctttatt   7200
gcttaatttt gctaattctt tgccttgcct gtatgattta ttggatgtt              7249

<210> SEQ ID NO 2
<211> LENGTH: 15
<212> TYPE: DNA
<213> ORGANISM: Artificial Sequence
<220> FEATURE:
<223> OTHER INFORMATION: Helper/Staple Strand Artificial Sequence

<400> SEQUENCE: 2
caatgctcat aaata                                                     15

<210> SEQ ID NO 3
<211> LENGTH: 15
<212> TYPE: DNA
<213> ORGANISM: Artificial Sequence
<220> FEATURE:
<223> OTHER INFORMATION: Helper/Staple Strand Artificial Sequence

<400> SEQUENCE: 3
ggaatcgttt aacag                                                     15

<210> SEQ ID NO 4
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 4
gaccataaag actgga                                                    16

<210> SEQ ID NO 5
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 5
cagcttgaca acagtt                                                    16

<210> SEQ ID NO 6
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 6
agaaaggatg ctttcg                                                    16

<210> SEQ ID NO 7
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 7
tatcagctac aactaa                                                    16

<210> SEQ ID NO 8
```

-continued

```
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 8 aatttttaa ggagcc                                                     16

<210> SEQ ID NO 9
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 9
ggctccaaca cgttga                                                    16

<210> SEQ ID NO 10
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 10 agaggggaa tactgc                                                     16

<210> SEQ ID NO 11
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 11
tagcgtccta atagta                                                    16

<210> SEQ ID NO 12
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 12
gttgcgccga caatga                                                    16

<210> SEQ ID NO 13
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 13
aggtgaattt cttaaa                                                    16

<210> SEQ ID NO 14
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 14
```

-continued

```
cgcataacta tcggtt                                                        16

<210> SEQ ID NO 15
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 15
tttaattgcg atatat                                                        16

<210> SEQ ID NO 16
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 16
caaaagaaaa ccaaaa                                                        16

<210> SEQ ID NO 17
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 17
acgataaagt tttgcc                                                        16

<210> SEQ ID NO 18
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 18
aaatgtttat cataac                                                        16

<210> SEQ ID NO 19
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 19
acagaggcta ccgata                                                        16

<210> SEQ ID NO 20
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 20
caacaaccat cggaac                                                        16

<210> SEQ ID NO 21
<211> LENGTH: 16
<212> TYPE: DNA
```

```
<213> ORGANISM: Artificial Sequence
<220> FEATURE:
<223> OTHER INFORMATION: Helper/Staple Strand Artificial Sequence

<400> SEQUENCE: 21
aagacagcat cgccca                                                    16

<210> SEQ ID NO 22
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 22
tcggtcgccg ggatcg                                                    16

<210> SEQ ID NO 23
<211> LENGTH: 16
<212> TYPE: DNA
<213> ORGANISM: Artificial Sequence
<220> FEATURE:
<223> OTHER INFORMATION: Helper/Staple Strand Artificial Sequence

<400> SEQUENCE: 23
cgcttttgtg aggctt                                                    16

<210> SEQ ID NO 24
<211> LENGTH: 32
<212> TYPE: DNA
<213> ORGANISM: Artificial Sequence
<220> FEATURE:
<223> OTHER INFORMATION: Helper/Staple Strand Artificial Sequence

<400> SEQUENCE: 24
gccaacagtc accttgctga acctgttggc aa                                  32
```

METHODS OF MAKING NUCLEIC ACID NANOSTRUCTURES

CROSS REFERENCE TO RELATED APPLICATIONS

This application claims priority under 35 U.S.C. §119 to U.S. Provisional Application Ser. No. 60/690,533, filed Jun. 14, 2005, the disclosure of which is incorporated herein by reference in its entirety.

STATEMENT REGARDING FEDERALLY SPONSORED RESEARCH

This invention was funded in part by a grant from the National Science Foundation (EIA-0093486 and CCF-0432193). The government may have certain rights in the invention.

TECHNICAL FIELD

The disclosure relates to methods and composition for generating nanoscale devices, systems, delivery compositions and nanoscale protein factories. More particularly, the invention relates to methods and compositions for generating nanoscale devices, circuits and systems from inorganic components and nanoscale patterning of biological entities such as enzymes.

BACKGROUND

The demand for ever-shrinking devices of ever-increasing complexity in areas from biomedicine to information technology has spurred several research efforts toward high-resolution, easy to manufacture nano-structures.

SUMMARY

The invention provides a method for producing a non-naturally occurring nucleic acid nanostructure. The method includes providing at least one structural unit, the unit comprising a single stranded polynucleotide scaffold; and a plurality of helper/staple strands each being designed to be at least partially complementary to the single stranded polynucleotide scaffold such that the helper/staple strands self anneal with the single stranded polynucleotide scaffold into a structural unit. The single-stranded polynucleotide scaffold is mixed with the plurality of oligonucleotide helper/staple strands to form a mixture. The mixture comprising the plurality of oligonucleotide helper strands are allowed to anneal, wherein a subset of oligonucleotide helper/staple strands are chosen to bind the polynucleotide scaffold in two or more positions and bring these separate regions of the polynucleotide scaffold together to form a desired bend in the polynucleotide scaffold and wherein a subset of the oligonucleotide helper/staple strands are chosen to have binding sites that constrain crossovers and contact points between helices to form desired angles commensurate with the helical twist of the chosen type of scaffold:helper/staple strand duplex. In one aspect, the helices of the polynucleotide are parallel and these parallel helices are constrained by a helper/staple strand crossovers and separated by a gap of about 2 nanometers. In yet a further aspect, a domain of the structural unit comprises parallel helices held together by a periodic pattern of crossovers spaced so that the distance between crossovers formed by two consecutive oligonucleotide helper/staple strands is an odd number of half turns apart. In yet another aspect, three adjacent parallel helices of a domain of the polynucleotide scaffold form an angle of 180 degrees and structural unit assumes a flat conformation. In another aspect, two or more individual domains of the structural unit are composed of parallel helices and the domains are non-parallel such that the domains have a defined angle between them. In another aspect, domains of the structural unit are connected by stacking interactions between blunt-ended helices and/or by helper strands that bridge helices of one domain to helices of another domain. In another aspect, the method generates a 3D structure, wherein at least two planar domains of a structural unit have parallel helices constrained to be at 90 degrees to each other, the helices of the first domain connected to the helices of the second domain by a set of crossovers that occur halfway between helper/staple strand crossovers of the first domain, an odd number of quarter turns from said crossovers. Where the domains of at least two domains of the polynucleotide scaffold have parallel helices they are held together by a pattern of crossovers spaced so that the distance between crossovers formed by the olignucleotide helper/staple strands is chosen according to the twist of the nucleic acid being used so that three adjacent parallel helices form an angle different than 180 degrees and the domain assumes a bent, corrugated or curved surface in 3D (the pattern can be periodic or non-periodic). The nanostructure may comprise DNA:DNA duplexes, DNA:RNA duplexes, PNA:DNA duplexes, and/or RNA:RNA duplexes. Where the nanostructure comprises DNA:DNA duplexes, a B-form of DNA is generated having a twist of about 10.5 basepairs per turn. Where the nanostructure comprises RNA:DNA and/or RNA:RNA duplexes an A-form of a duplex is generated having a twist of about 11 basepairs per turn. Crossovers formed by the helper/staple strand in the nanostructure may be parallel or anti-parallel. In another aspect, the nanostructure is a cage for another type of molecule and a wall of the cage is actuated to open and close by the plurality of extra olignucleotides. The nanostructure may comprise single stranded sections that can be used to capture of the nanostructure by an oligonucleotide probe complementary to the single-stranded region for purification of the nanostructure. A large stoichiometric excess of about 10 to 300 fold of oligonucleotide helper/staple strands can be used to generate the nanostructure.

The invention also provides a nanostructure generated by the method of the invention.

The invention also provides living organisms comprising a nanostructure of the invention either produced in vivo or delivered to the living organism. In one aspect, the nanostructure interacts with the cytoskeleton and or cell membrane of the living organism thereby affecting the organism's shape or affecting its growth or movement.

The invention also provides a method of designing an arbitrary nucleic acid structure comprising threading a substantially known single stranded polynucleotide scaffold sequence in a predetermined design; generating a block diagram comprising a selected number of half-turns of the single stranded polynucleotide scaffold sequence; identifying one or more scaffold crossovers in the polynucleotide scaffold when threaded; generating a plurality of oligonucleotide helper/staple strand sequences to complement the scaffold strands, wherein the plurality of oligonucleotide helper/staple strand sequences are at least partially complementary to the polynucleotide scaffold sequence wherein a subset of oligonucleotide helper/staple strands are chosen to be at least partially complementary to the polynucleotide scaffold sequence in two or more positions and bring these separate regions of the polynucleotide scaffold together to form a desired bend in the polynucleotide scaffold sequence and wherein a subset of the oligonucleotide helper/staple strands sequence are chosen to have binding sites that constrain crossovers and contact points between helices to form desired angles commensurate with the helical twist of the chosen type of scaffold:helper/staple strand duplex. The method can be implemented by a computer and/or over the internet.

The invention further provides method of incorporating/attaching a desired composition to a scaffolded nucleic acid nanostructure of the invention. In one aspect, an agent or compound is linked to the nucleic acid nanostructure of the invention using an intercalating agent. Accordingly, the invention provides scaffolded nucleic acid nanostructure that can incorporate a nanoparticle and/or a biological agent. The nanostructure is thus useful for the formation of nano-circuits, sensors, delivery agents and the like.

The invention also provide a nucleic acid nanostructure comprising at least one unit, the unit comprising, a single scaffold polynucleotide strand scaffold; and a plurality of helper/staple strands each being designed to be at least partially complementary to the single stranded polynucleotide scaffold such that the helper/staple strands self anneal with the single stranded polynucleotide scaffold into a structural unit, wherein a subset of oligonucleotide helper/staple strands are chosen to bind the polynucleotide scaffold in two or more regions and bring these separate regions of the polynucleotide scaffold together to form a desired bend in the polynucleotide scaffold and wherein a subset of the oligonucleotide helper/staple strands are chosen to have binding sites that constrain crossovers and contact points between helices to form desired angles commensurate with the helical twist of the chosen type of scaffold:helper/staple strand duplex.

The details of one or more embodiments of the disclosure are set forth in the accompanying drawings and the description below. Other features, objects, and advantages will be apparent from the description and drawings, and from the claims.

DESCRIPTION OF DRAWINGS

FIG. 7A-B depicts (A) one type of circuit that can be generated using the methods and compositions of the invention. Optical elements can be associated with a scaffolded nucleic acid origami (which might be flourophores or quantum dots). Information would then be processed by a circuit (composed of small molecule switches, gold nanoparticles, flourophores, quantum dots and/or the like). (B) depicts an enzyme factory. Three proteins, A, B, and C are attached to a scaffolded nucleic acid origami in an arrangement so that they can act on three chemical monomers (say stars, squares, and hexagons, respectively for proteins A, B, and C) and polymerize them into long chains. The positions of the proteins A, B, and C dictate the order of the monomers in the final polymer. Scaffold nucleic acid origami can also generate gene chips located within cells or provide "artificial centrosome" made from scaffolded nucleic acids.

DETAILED DESCRIPTION

Figure 1:
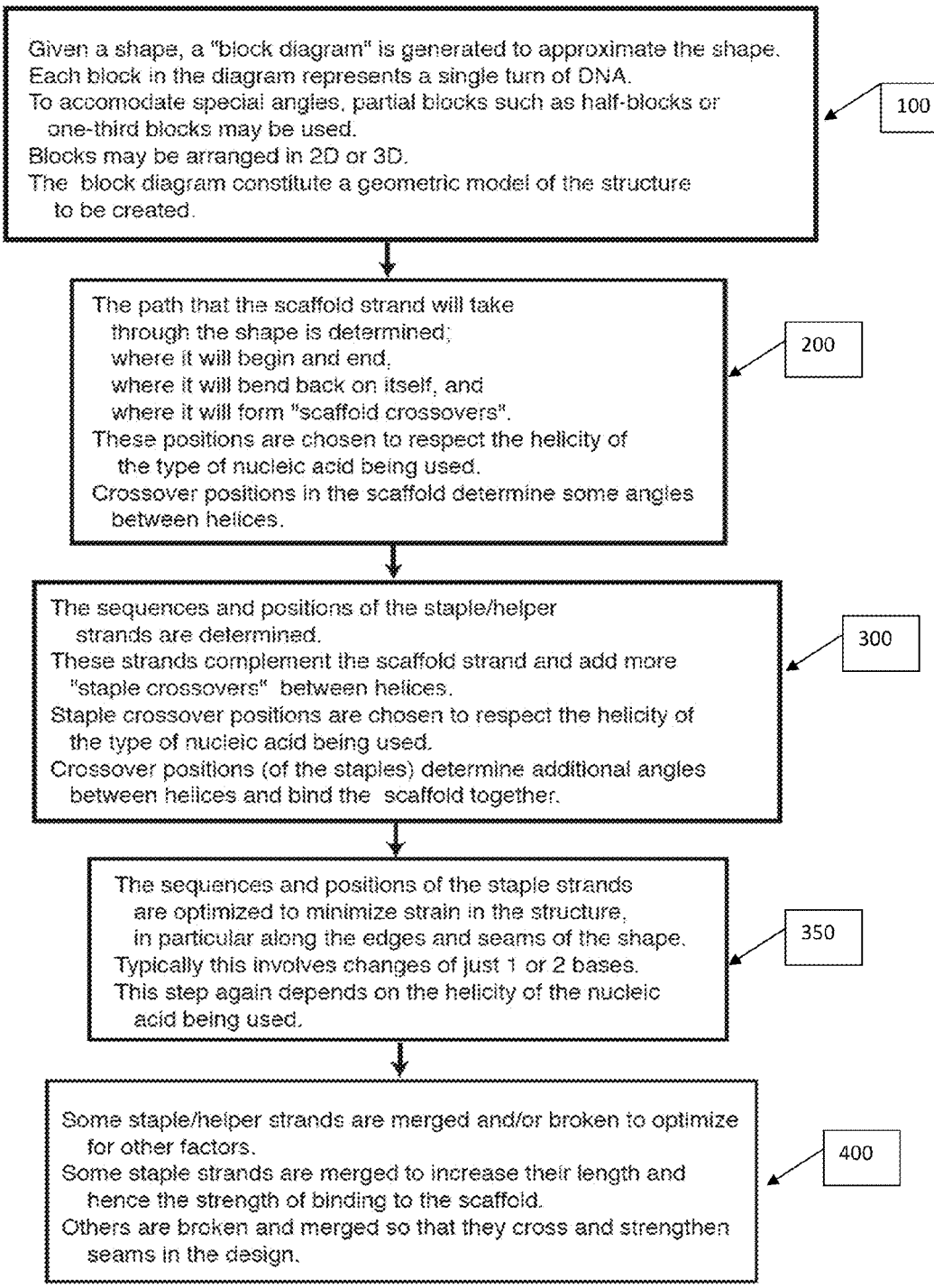
FIG. 1 shows a general flow process for generating an arbitrary nanostructure from nucleic acids.

As used herein and in the appended claims, the singular forms "a," "and," and "the" include plural referents unless the context clearly dictates otherwise. Thus, for example, reference to "a polynucleotide" includes a plurality of such polynucleotides and reference to "the helper strand" includes reference to one or more helper strands known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The invention provides a versatile and simple method for using numerous short single strands of nucleic acids (helper strands) (e.g., DNA) to direct the folding of a long, single strand of polynucleotide (scaffold strand) into desired shapes that are roughly 100 nm in diameter and have a spatial resolution of about 6 nm. This process is referred to herein as nucleic acid scaffolding, or scaffolded nucleic acid origami. The invention provides the ability to generate nucleic acid scaffold shapes on the order of about 100-nm to a micron or more in having a complexity that is ten-fold higher than that of any previously self-assembled arbitrary pattern and comparable to that achieved using AFM and STM surface manipulation.

The resolution achieved by the methods and compositions of the invention is much smaller than the resolution currently used in micro/nanofabrication for computer chips and other devices (e.g., 90 nanometers for photolithography), and thus has great potential for the creation of nanostructures (for computers or other devices). Further, because the method uses a bottom-up approach (self-assembly) it is extremely simple because it does not require expensive equipment or a clean room to perform and thus may be less expensive and faster than top-down methods such as atomic force microscopy or scanning tunneling microscopy.

Scientists have produced two-dimensional patterns from DNA, but the process is complicated and the yields are often low. The invention provides a simple and efficient method of arranging polynucleotides into desired shapes and structures. Such methods and compositions are useful in a wide-range of areas from electrical engineering, material sciences to biotechnology, enzyme factories, and diagnostics.

The exquisite specificity of Watson-Crick base pairing allows a combinatorially large set of nucleotide sequences to be used when designing binding interactions. The field of 'DNA nanotechnology' has exploited this property to create a number of more complex nanostructures, including two-dimensional arrays with 8-16 unique positions and less than 20 nm spacing, as well as three-dimensional shapes such as a cube and truncated octahedron. However, because the synthesis of such nanostructures involves interactions between a large number of short oligonucleotides, the yield of complete structures is highly sensitive to stoichiometry (the relative ratios of strands). The synthesis of relatively complex structures was thus thought to require multiple reaction steps and purifications, with the ultimate complexity of DNA nanostructures limited by necessarily low yields.

The invention provides scaffolded self-assembly of nucleic acid strands and methods to create arbitrary shapes and patterns of nucleic acids at the nanoscale level. Prior attempts at scaffolded assembly have failed to create arbitrary shapes or patterns. In particular, the use of long DNA scaffolds in combination with hundreds of short strands, as in the invention, has been inhibited by several misconceptions: it was assumed that (1) sequences must be optimized to avoid secondary structure or undesired binding interactions, (2) strands must be highly purified, and (3) strand concentrations must be precisely equimolar. These three criteria are important for the formation of many DNA nanostructures and yet all three are not required in the methods of the invention. For example, M13mp18 is essentially a natural polynucleotide that has a predicted secondary structure which is more stable (lower in energy) than similar random sequences (as used for exemplary purposes in the Examples below). Further, stocks of staples (e.g., short oligonucleotides) were used successfully at stoichiometries that varied over an order of magnitude. The invention thus allows the creation of nanostructures in high-yield (typically greater than 70%) but does so quickly and easily without a requirement for specially designed scaffolds or extensive purification.

The invention is based in part upon the fact that oligonucleotide/polynucleotide crossovers may be used to hold helices rigidly in a parallel orientation. More specifically, wherever the twist of two parallel helices bring the backbones of the two helices sufficiently close, reciprocal strand exchange can be used to add a crossover. Furthermore, such a crossover does not disturb base pairing in either helix; the crossover is envisioned to contain only a single phosphate from each strand.

The composition of double crossovers into periodic two dimensional crystals showed that, through the use of sticky-end interactions, arbitrary numbers of helices could be held in a parallel arrangement by crossovers. Because the natural equilibrium length for a single turn of DNA appears to be close to 10.5 base pairs, and because DNA backbones are not symmetrically spaced around the helix (there is a major and minor groove), designs of such two dimensional DNA nanostructures (which use integral numbers of DNA bases) invariably incorporate features that should cause strain. That is, the design assumes a DNA geometry slightly different than that of a single isolated helix with 10.5 bases per turn with 'normal' major/minor groove angles. For example, a number of 2D DNA nanostructures form tubes rather than sheets. It is noted that other nucleic acids may be used in the methods and compositions of the invention. The helical turn of such nucleic acid are slightly different. For example, DNA:RNA and RNA:RNA about 11 bases per turn in A-form; DNA:PNA about 13 bases; and PNA:PNA about 18 bases. Furthermore, the helical twist distance in bases will vary based upon hydration (e.g., DNA:DNA helical distance is about 11 bases when dehydrated). One of skill in the art will be able to identify the base distance per helical turn. Given any homo- or heteroduplex nucleic acid formations, one of skill in the art will be able to determine the number of bases that bases per helical twist.

Besides the difficulty of keeping track of thousands of DNA bases, the greatest difficulty in design of DNA origami (and the greatest motivation for computer-aided design) is dealing with the helical nature of DNA. In particular, determining where to position crossovers so that they fall as close as possible to the tangent between parallel helices requires keeping track of two features of DNA's helical geometry. First considered is the angular twist of the helix per base of DNA helix, often expressed as the number of bases per 360 degree turn. The form of DNA used here (and in most DNA nanotechnology) is B-DNA; when it occurs as a free double helix it has roughly 10.5 bases per turn. Constrained in a DNA nanostructure, it can occur in a slightly overtwisted (>10.5 bases per turn) or undertwisted (<10.5 bases per turn) state.

Second considered is the fact that the DNA double helix is an asymmetric helix-the two backbones from which complementary bases project into the center of the helix are not symmetrically spaced around the roughly circular cross section of the helix. This gives DNA its characteristic 'major groove' and 'minor groove'; if one draws rays from the center of the DNA helix to the backbones of the DNA strands, the smaller angle subtended by the rays is the minor groove. If the DNA helix were a simple helix, with continuous rather than discrete strands and symmetric placement of the strands around a helix, then it would be possible to introduce a crossover along the tangent line between two parallel helices whenever a pair of strands from different helices crossed through the tangent line at the same point.

A solution provided by the invention is that crossovers (and nicks) in extended structures of parallel helices are placed so that they have symmetries which balance strain. For scaffolded nucleic acid origami this criterion was used in the placement of crossovers. The use of 16 bases to represent 1.5 turns of DNA (in the 1.5-turn crossover spacing structures) or 26 bases to represent 2.5 turns of DNA (in the 2.5-turn crossover spacing structures) means that the helical domains between crossovers are slightly over twisted or under twisted, respectively. A domain of a scaffold polynucleotide will typically refer to an odd number of half-turns of the polynucleotide scaffold. To balance this strain, alternating columns of helper crossovers are related by a glide symmetry; the local configuration of crossovers in one column is identical to that of crossovers in the next column after a translation and a 'ip' (a rotation about one of the crossovers in-plane axes). Cross-section Z of FIG. 2a shows the presumed orientation of backbones through one column of crossovers in the lattice, and cross-section W, the presumed orientation of crossovers in an adjacent column 1.5 turns away. This symmetry tends to balance strain in the origami structures.

If two helices were properly aligned, it would seem that this opportunity would happen at a sequence of points spaced successively one turn apart along the helices. However, the combination of the nonintegral number of bases per turn and the existence of a major/minor groove mean that the backbone of the DNA strands cannot always be positioned exactly at the tangent point between two adjacent helices.

The twist of two backbones at the position of closest approach to this tangent line could be off by roughly 34 degrees (in each helix) and can introduce undesired strain into the structure. Just keeping track of the point of closest approach is difficult to do by hand; humans don't naturally think in terms of a double helix, made worse by the fact that it is asymmetric. (The sign of the error in twist is determined by the right-handed nature of DNA, and it is easy to flip in mental manipulations.) The use of a regular array of crossovers makes the problem somewhat better-the configuration of twists can be determined for one crossover and understood at other locations by using the symmetries of the crossover lattice. Edges and seams of DNA origami present departures from the regular lattice and the twist at such locations is best kept track of by software.

Design of scaffolded nucleic acid origami generally comprises building a geometric model of a nucleic acid structure that will approximate the desired shape/geometry. FIG. 3a shows an example shape that is 33 nm wide and 35 nm tall. The shape is filled from top to bottom by an even number of parallel double helices, idealized as cylinders. The helices are cut to fit the shape in sequential pairs and are constrained to be an integer number of turns in length. To hold the helices together, a periodic array of crossovers (indicated in FIG. 2a as small crosses) is incorporated; these crossovers designate positions at which strands running along one helix switch to an adjacent helix and continue there. The resulting model approximates the shape within one turn (3.6 nm) in the x-direction and roughly two helical widths (4 nm) in the y-direction. DNA lattice parallel helices in such structures are not close-packed, perhaps owing to electrostatic repulsion. Thus, the exact y-resolution depends on the gap between helices. The gap, in turn, appears to depend on the spacing of crossovers. In FIG. 2a crossovers occur every 1.5 turns along alternating sides of a helix, but any odd number of half-turns may be used.

The basic technique for creating shapes involves folding a long single stranded polynucleotide, referred to herein as a "scaffold strand", into a desired shape or structure using a number of small "helper strands" as glue to hold the scaffold in place. The number of helper strands will depend upon the size of the scaffold strand and the complexity of the shape or structure. For example, for relatively short scaffold strands (e.g., about 150 to 1500 base in length) and/or simple structures the number of helper strands may be small (e.g., about 5, 10, 50 or more). For longer scaffold strands (e.g., greater than 1500 bases) and/or more complex structures, the number of helper strands may be several hundred to thousands (e.g., 50, 100, 300, 600, 1000 or more helper strands).

The methods of the invention use short "staple" strands or "helper strands" of nucleic acids to fix a polynucleotide strand into a particular pattern. The choice of staple strands determines the pattern. In one aspect, a software program is used to identify the staple strands needed to form a given design.

The invention provides methods for creating any desired shape or structure out of a polynucleotide. Once the shape or structure has been created, any desired pattern or ligand may be added to the shape or structure. For example, a triangular structure can be created, and then the numbers 1, 2, and 3 can be added to the arms to differentiate them. In another aspect, a rectangle can be made, and a map of the western hemisphere can be added to the rectangular structure. The resolution of the shapes or structures is about 6 nanometers in one direction and about 3 nanometers in the other. For example, with internal labels on helper/staple strands the resolution can be reduced to about 3 nm. This means that, given a desired geometric structure, a polynucleotide structure can be made that matches the contours to within better than 6 nanometers. After the desired structure has been generated, additional patterns, materials or structures can be added with approximately 6 nanometer resolution.

Several factors contribute to the success of scaffolded nucleic acid origami of the invention. These are (1) strand invasion, (2) an excess of staples, (3) cooperative effects and (4) design that intentionally does not rely on binding between staples. Briefly, strand invasion allows correct binding of excess full-length staples to displace unwanted secondary structure, incorrect staples, or grossly truncated staples. Further, each correct addition of a staple organizes the scaffold for subsequent binding of adjacent staples and precludes a large set of undesired secondary structures. Last, because staples are not designed to bind one another, their relative concentrations do not matter.

The method presented by the invention is easy to implement, provides high yield and is relatively inexpensive. For rigid designs using circular scaffolds (rectangles with patterns, three-hole disks, and sharp triangles), yields of qualitatively well-formed structures were at least 70%.

The invention provides a process for designing arbitrary nanoscale structure utilizing nucleic acids. Referring to FIG. 1 there is shown a flow diagram depicting a process of the invention. At box 100 a diagram of the desired nanostructure is generated using a box diagram wherein each box represents a desired number of quarter, thirds or half-turns of a scaffold strand of polynucleotide. This process may be carried out manually (e.g., by hand) or via computer. In 100 a geometric model of a nucleic acid (e.g., DNA) structure is built that approximates the desired shape or configuration. The desired shape may be 2D or 3D. FIG. 3a shows an example shape that is 33 nm wide and 35 nm tall. In the shape depicted in FIG. 3a, an even number of parallel double helices, idealized as cylinders is shown. FIG. 3a depicts the helices cut to fit the shape in sequential pairs and are constrained to be an integer number of turns in length. A scaffold polynucleotide comprising a known sequence is then threaded into the design manually or via computer implemented methodology (200). Each 180° turn in the nucleic acid design is characterized by a height of at least 2 helices. Scaffold crossovers regions are identified based upon the polynucleotide sequence.

The process utilizes an inter-helix gap of 1 nm for 1.5-turn spacing and 1.5 nm for 2.5-turn spacing, yielding a y-resolution of 6 or 7 nm, respectively. Each 180 degree turn in the scaffold strand encompasses the width (e.g., the distance between the resulting strands) of about two helices (e.g., plus an inter-helix gap between the helices). Conceptually, 200 (illustrated in FIG. 2b) proceeds by folding a single long scaffold strand (e.g., 900 nucleotides (nt) in FIG. 2b) back and forth in a raster fill pattern so that it comprises one of the two strands in every helix; progression of the scaffold from one helix to another creates an additional set of crossovers, the 'scaffold crossovers' (indicated by small crosses in FIG. 2b). A constraint on a folding path is that the scaffold can form a crossover only at those locations where the nucleic acid twist places it at a tangent point between helices. Thus for the scaffold to raster progressively from one helix to another and onto a third, the distance between successive scaffold crossovers must be an odd number of half turns. Conversely, where the raster reverses direction vertically and returns to a previously visited helix, the distance between scaffold crossovers must be an even number of half-turns. Note that the folding path shown in FIG. 2b is compatible with a circular scaffold and leaves a 'seam' (a contour which the path does not cross).

The scaffold strand is best imagined as a long piece of string. To make a shape or structure the scaffold strand is folded back and forth, in a raster pattern, to define the shape or structure. The resulting path that the scaffold strand takes is somewhat like a path in a maze; it typically does not cross itself. Each fold of the scaffold strand has a length which is a multiple of half turns of a polynucleotide (e.g., DNA) (about 5 or 6 nucleotides). Each fold occurs on a particular row in a shape or structure that is being created. If the fold is an even number of half turns the scaffold reverses direction in the shape/structure; if the fold is an odd number of half turns the scaffold continues the same direction in the shape/structure. These rules are typical for the flat 2D structures demonstrated in the specific examples below. For 3D structures the lengths of helices may be different. For example, to create a raster of the scaffold arrayed on a rectilinear 3D grid then the length of the scaffold may be in multiples of one-quarter (¼) turns. Similarly to create a raster of the scaffold on a hexagonally arrayed 3D grid the length of the scaffold may be in multiples of one-third (⅓) turns. By "arrayed on a type-X 3D grid," is meant that the positions of the centers of the helices in a cross-section of the nanostructure which is taken to be perpendicular to the set of parallel helices would lie a 2D pattern that could be aligned with an type-X 2D grid.

When the scaffold strand is folded into a shape or structure, certain sections of the scaffold are close together—sections that would be far away if the scaffold strand were completely stretched out. For every short section of the scaffold strand (e.g., 8 bases), the computer program determines what other section of the scaffold should be nearby in the completed shape or structure. A computer program of the invention can then design helper strands to tie close or juxtaposed sections together. Imagine one section of a scaffold, strand 'A', that passes close to another section of a scaffold, strand 'B' (strands 'A' and 'B' may be the same of different scaffold strands). The program designs a helper strand so that half the helper strand binds 'A', and the other half of the helper strand binds 'B', when the helper strand binds both 'A' and 'B', the helper strand ties the strands together.

Given the folding path for the scaffold to form a desired shape or structure, the appropriate helper strands to hold it together are selected (300; see FIG. 1). For complex shapes, a computer program is typically used to select the helper strands. Helper strands are designed to hold two or more small sections or domains of the scaffold strand together.

Figure 2C:
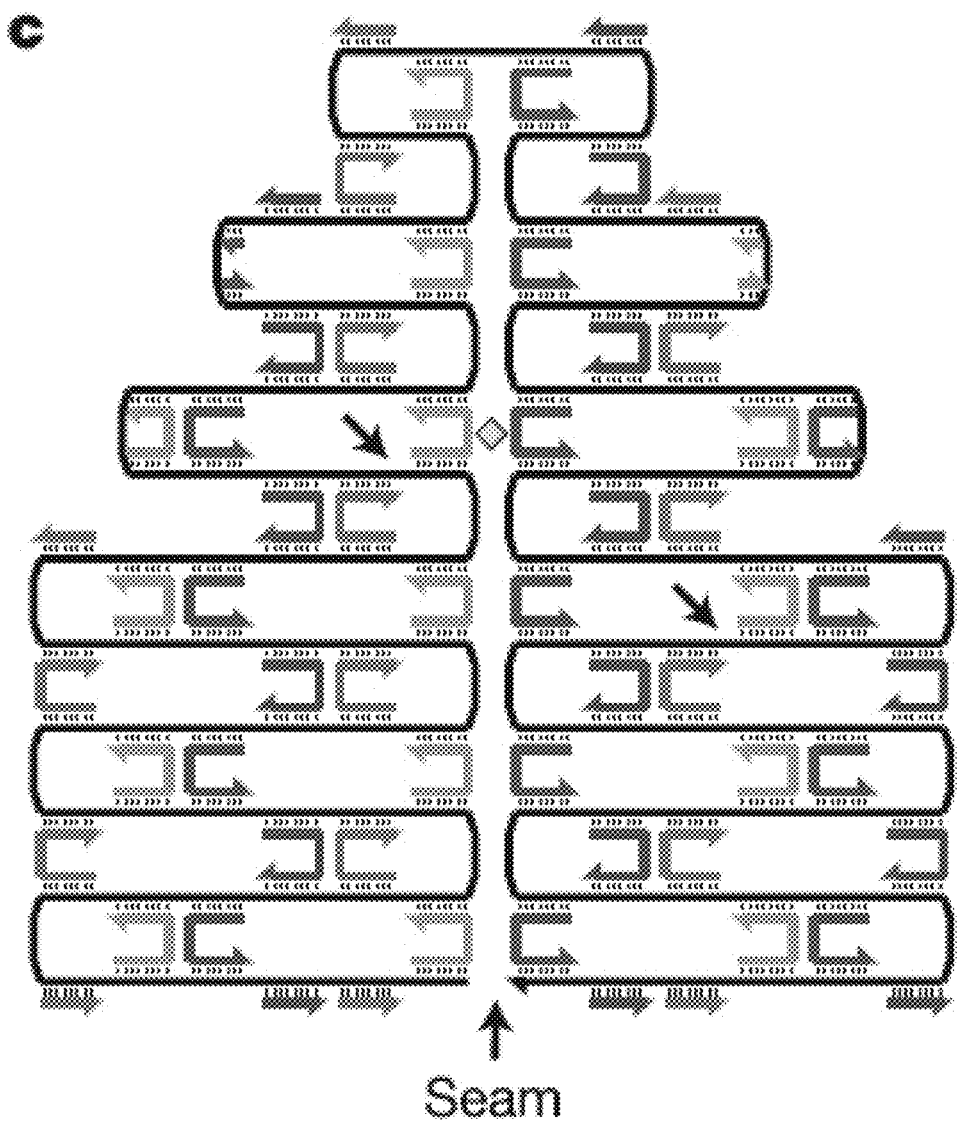
FIG. 2 shows a DNA design A) A shape (5) approximated by parallel double helices joined by periodic crossovers (10). B) A scaffold runs through every helix and forms more crossovers (10). C) As first designed, most helper strand/staples bind two helices and are 16-mers. D) Similar to (C) with strands drawn as helices. Gray triangles point to scaffold crossovers, black triangles to periodic crossovers with minor grooves on the top face of the shape, hatched triangles to periodic crossovers with minor grooves on bottom. Cross sections of crossovers (1, 2, viewed from left) indicate backbone positions with lines, and major/minor grooves by large/small angles between them. Arrows in (C) point to nicks sealed to create strands in (D). Diamonds in (C) and (D) indicate a position at which staples may be cut and resealed to bridge the seam. (E) A finished design after merges and rearrangements along the seam. Most staples are 32-mers spanning three helices. Insets show a dumbbell hairpin (D) and a 4-T loop (E), modifications used in FIG. 4.

A plurality of oligonucleotide helper strands are then designed based upon the known polynucleotide sequence (300). Once the geometric model and a folding path are determined, the design is represented as a list of nucleic acid strand lengths and offsets in units of half turns. These lists, along with the sequence of the actual scaffold to be used, are optimized (350). Rather than assuming 10.5 base pairs (bp) per turn (which corresponds to standard B-DNA twist), the program uses an integer number of bases between periodic crossovers (e.g., 16 bp for 1.5 turns). The process then continues by designing a set of 'staple strands' (see, e.g., the strands in FIG. 2c) that provide Watson-Crick complements for the scaffold and create the periodic crossovers. Staples, in some instances, reverse direction at these crossovers; thus some crossovers are antiparallel, a stable configuration well characterized in DNA nanostructures. Note that the crossovers depicted in FIG. 2c are drawn somewhat misleadingly, in that single stranded regions appear to span the inter-helix gap even though the design leaves no bases unpaired. (The use of parallel junctions which are less stable in structures composed only of short oligonucleotides can be stabilized by the long scaffold strand and thus can be used as well.)

Typically each turn is representative of a nucleic acid helix wide and a pair of nucleic acid helices in height. The aspect ratio of the block used is determined based on the inter-helix gap expected for the spacing of crossovers that will be used. To hold the helices together, a periodic array of crossovers (indicated in FIG. 2a as small crosses (10)) is incorporated; these crossovers designate positions at which strands running along one helix switch to an adjacent helix and continue there. The resulting model approximates the shape within one turn (3.6 nm) in the x-direction and roughly two helical widths (4 nm) in the y-direction. Nucleic acid lattice parallel helices are not close-packed, perhaps owing to electrostatic repulsion. Thus, the exact y-resolution depends on the gap between helices. The gap, in turn, appears to depend on the spacing of crossovers. In FIG. 2a crossovers occur every 1.5 turns along alternating sides of a helix, but any odd number of half-turns may be used.

In the assembled structures, helices are likely to bend gently to meet at crossovers so that only a single phosphate from each backbone occurs in the gap. Such small-angle bending is not expected to greatly affect the width of the origami structure. The minimization and balancing of twist strain between crossovers is complicated by the non-integer number of base pairs per half-turn (5.25 in standard B-DNA) and the asymmetric nature of the helix (it has major and minor grooves). Therefore, to balance the strain caused by representing 1.5 turns with 16 bp, periodic crossovers are arranged with a glide symmetry, namely that the minor groove faces alternating directions in alternating columns of periodic crossovers (see FIG. 2d, especially cross-sections 1 and 2). Scaffold crossovers are not balanced in this way. The twist of scaffold crossovers is calculated and their position is changed (typically by a single bp) to minimize strain; staple sequences are recomputed accordingly. Along seams and some edges the minor groove angle (150°) places scaffold crossovers in tension with adjacent periodic crossovers (FIG. 2d, cross-section 2); such situations are left unchanged.

Figure 2D:
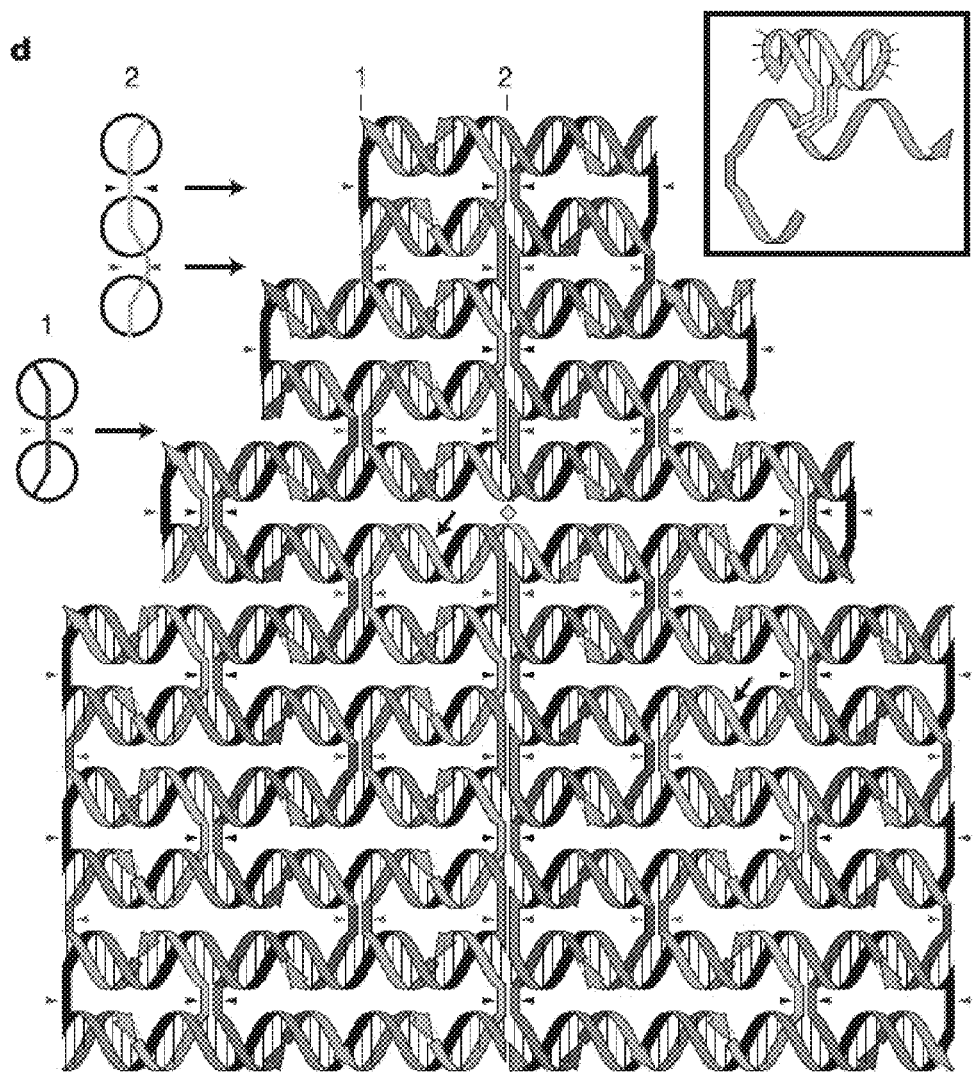
Figure 2E:
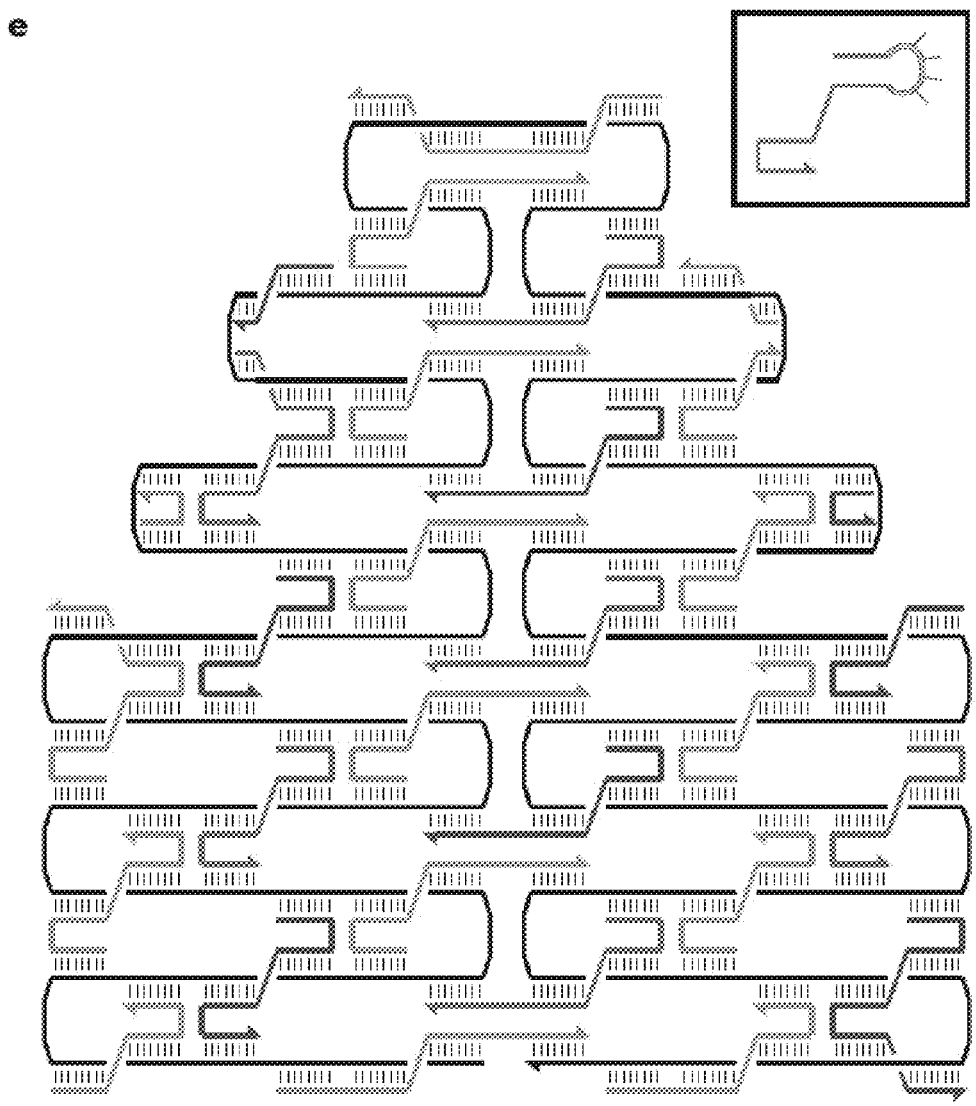

Wherever two staples meet there is a nick in the backbone. Nicks occur on the top and bottom faces of the helices, as depicted in FIG. 2d. To give the staples larger binding domains with the scaffold (in order to achieve higher binding specificity and higher binding energy which results in higher melting temperatures), pairs of adjacent staples are merged across nicks to yield fewer, longer, staples (FIG. 2e). To strengthen a seam, an additional pattern of breaks and merges may be imposed to yield staples that cross the seam; a seam spanned by staples is termed 'bridged'. The pattern of merges is not unique; different choices yield different final patterns of nicks and staples. All merge patterns create the same shape but, as shown later, the merge pattern dictates the type of grid underlying any pixel pattern later applied to the shape.

The use of a glide symmetry means that large regions of a scaffolded nucleic acid origami should have balanced strain. However, at seams and edges this is not necessarily true, even where a seam or edge lines up with the underlying crossover lattice. At seams or edges, because nucleic acids have a major and minor groove, a crossover involving helper strands is in tension with an adjacent crossover involving the scaffold strand. Such a configuration of crossovers in tension has never before been used in DNA nanostructures. In FIG. 1D the cross section through a seam has been drawn so that the helper crossover is relaxed and the scaffold crossover is highly strained. Both crossovers can assume some intermediate conformation. Strain at seams or edges does not appear to cause any gross defects in the origami; bases at the end of the helices are highly available for stacking against other scaffolded nucleic acid origami which suggests that the last base pair does form and assumes a planar configuration. If, in the future, strain associated defects should be detected at edges, then one or two scaffold bases could be left unpaired and allowed to form a hairpin that should relax the crossover.

Another place that the design of DNA origami currently breaks with normal DNA nanotechnology is in its use of a wide range of sequences for its anti-parallel crossovers. Customarily, crossover sequences are drawn from one of a few sequences that both form an immobile branched junction and have well-characterized geometry. Such junctions have been designed with minimal symmetry so that the junction cannot branch migrate back and forth. In the invention such constraints on the junctions have been ignored. They may be added to a design but the demonstration of the invention shows that the use of particular junction sequences is unnecessary.

Helper strands can also be designed to tie 3 or more nearby sections of the scaffold strand together. Generally, a helper strand is complementary to at least two regions of the scaffold strand. Generally, the helper strand has a region of at least 6 nucleotides that are complementary to corresponding regions of a scaffold strand. The entire helper strand will generally be at about 6 to 60 nucleotides in length. The complementary regions on the scaffold can be adjacent or not adjacent. In one embodiment, the helper strand is complementary to three regions of the scaffold. For example, a helper strand can be used that has regions complementary to three regions, and has complementary regions of 8, 16 and 8 nucleotides respectively with no intervening spacer nucleotides between the complementary regions. Along the edges or seams that occur in a shape or structure, some helper strands can be used that bind only a single region of the scaffold strand. Such helper strands aid in stiffening the shape or structure.

In the examples discussed herein, the particular scaffold strand used to demonstrate the method is 7249 base long genomic DNA of the virus m13, but any essentially random polynucleotide strand may be used. The helper strands are shorter, typically 6-60 bases long (e.g., 10-30 bases long), and may be inexpensive, unpurified, synthetic nucleic acid polymers.

Perfect Watson-Crick binding is only an idealization. Helper strands inevitably bind to places on the scaffold to which they are not a perfect match. If an incorrectly bound helper strand has a run of several mismatches with the scaffold at such an imperfect site, there is a mechanism called 'strand displacement' by which the correct helper strand for the site can gain a foothold at these mismatches, and displace the incorrect helper strand. This mechanism plays a role in displacing unintended matches in scaffold nucleic acid origami.

The scaffold strand itself may have self complementary regions that cause the strand to fold on itself in what is known as 'secondary structure'. Accordingly in one aspect of the invention such secondary structures are predicted and removed appropriately (e.g., by cleaving out the structure with a nuclease and then ligating the scaffold strand back together using common molecular biology techniques). For example, such secondary structures can be predicted with computer programs, such as Michael Zuker's Mfold server. In another aspect of the invention, if the secondary structure of the scaffold strand is not too great, then it may be ignored and not removed. As described in the Examples below, M13mp18 has a 20 base-pair long hairpin that is not merely predicted, it is known to have biological significance for the virus life cycle. Because the hairpin's region of complementarity is longer than any single helper-scaffold binding domain, the hairpin is avoided and left in the unfolded leftover sequence. In the specific examples provided herein for the generation of a scaffolded nucleic acid origami structure a natural sequence for the scaffold strand (the M13mp18 viral genome) was used because it was cheaply and easily available. However, other polynucleotide scaffold strands can be used. In fact, it is the normal practice of DNA nanotechnology to optimize polynucleotides to avoid unintended binding events. Accordingly, other scaffold polynucleotides (either synthetic or naturally occurring) can be obtained/designed to avoid undesirable interactions between helper strand and scaffold strand, between helper strand and helper strand, or between the scaffold strand and itself. Such optimization will be useful as larger DNA origami's are constructed and sequence repetition becomes a more challenging problem. If some portion of the scaffold is not used to form the shape, a set of extra strands, called remainder strands, can be used that bind to regions of the unused portion of the scaffold. Unused portions of the scaffold can be left single-stranded to allow, for example, the combination of scaffolded nucleic acid origami into larger shapes, or capture of scaffold nucleic acid origami by oligonucleotide probes for purification.

Once the helper strands are designed, they are synthesized, mixed with the scaffold strand in a buffer solution, heated (for example to about 90 degrees centigrade), and cooled to room temperature. The buffer solution will be selected to allow for hybridization of the scaffold strand and helper strands. In one embodiment, the buffer comprises magnesium. Generally a stoichiometric excess of the helper strands is used. In one embodiment, 10-100 times as many helper strands are present as would be needed to fold all the scaffold strands. Typically, the structures are folded in solution and applied to a substrate after they have been formed. Where the shape or structure is a two dimensional shape or structure, the solution of scaffold and helper strands is applied to a substrate after annealing. In one embodiment, the substrate is mica.

Accordingly, the method of the disclosure comprises inputting a representation of a geometrical model, any seams in the structure, folding path that runs through the model and a sequence for the scaffold. Using one of a couple different (but equally low-level representations) the model, seam positions, and folding path are input as lists of helix lengths in units of turns or bases. The folding path uses an additional list of orientations specifying its direction of travel to the left or right of adjacent seams. The design method (which may be computer implemented) applies the scaffold sequence to the model, using the folding path as a guide, and generates the appropriate set of helper strands. Similar to Latex, the program is run several times to make various refinements to the design, for example, to change the position of crossovers by a single base to minimize twist strain, or to join or to break helper strands. Like the geometrical model and folding path, these perturbations to the structure are decided by the user and specified in detail.

Thus there are several opportunities to further modify automation of the design software. Users can specify a shape and the software can generate the best-fit geometrical model that approximates the shape within a single turn of DNA. Further, a generalization of some raster-fill algorithm can be used to generate the folding path and seam positions, to route the scaffold strand appropriately around voids in the specified shape. Because the folding path is not unique and different folding paths may have bearing on the mechanical properties of the final structure through the placement of seams, the raster-fill algorithm should take some user preferences concerning the placement of seams and routing around voids. The adjustment of crossover positions to relieve strain should be similarly automatic and similarly subject to some user preference. On the edges of a shape some twist strain may be acceptable in order to better approximate a desired curve; within a shape, strain along seams should be avoided if possible and optimization calculated. Similarly, the merging of helper strands into longer sequences, or rearrangement of helper strands to bridge seams, should be automated. Users should be able to specify one of several patterns of merges that can be applied; intervention should only be required where seams or edges generate unusual boundary conditions. And the design program can have a WYSIWYG interface that can render the design as a line drawing, a two-dimensional drawing of helices or full 3D model of the structure. 3D modeling tools for nanocanonical DNA structures (like DNA origami) exist but none have ever been integrated into a DNA design package. All of the above modifications are implementable, and contain little in the way of fundamental algorithm development.

The application of scaffolded nucleic acid origami to three dimensions is also contemplated by the invention. There are several simple three dimensional generalizations of scaffolded nucleic acid origami as described here. That is, there are several distinct geometrical contexts (that occur in 2D DNA origami) where one might add joints to two dimensional origami and which force the folding path into the third dimension. Further, in each context, there are several types of joints that one might consider, based upon which generalizations will fold most robustly and yield rigid 3D structures. For example, new ideas for better 3D joints and the composition of domains into larger 3D structures will inevitably come from playing with a 3D DNA origami computer interface and environment. Even in the absence of such a program, an obvious 3D generalization of the current embodiment of the invention is to create perpendicular planes of scaffolded nucleic acid origami. To connect one raster-fill domain A in a perpendicular fashion to a raster domain B, helper strands along an edge of A may be connected to B by crossover points that are halfway between the normal in-plane set of crossovers of domain B. Because of the glide symmetry present in the current embodiment, these crossovers should occur exactly on the face of domain B and hold domain A rigidly and perpendicularly to domain B.

Figure 6:
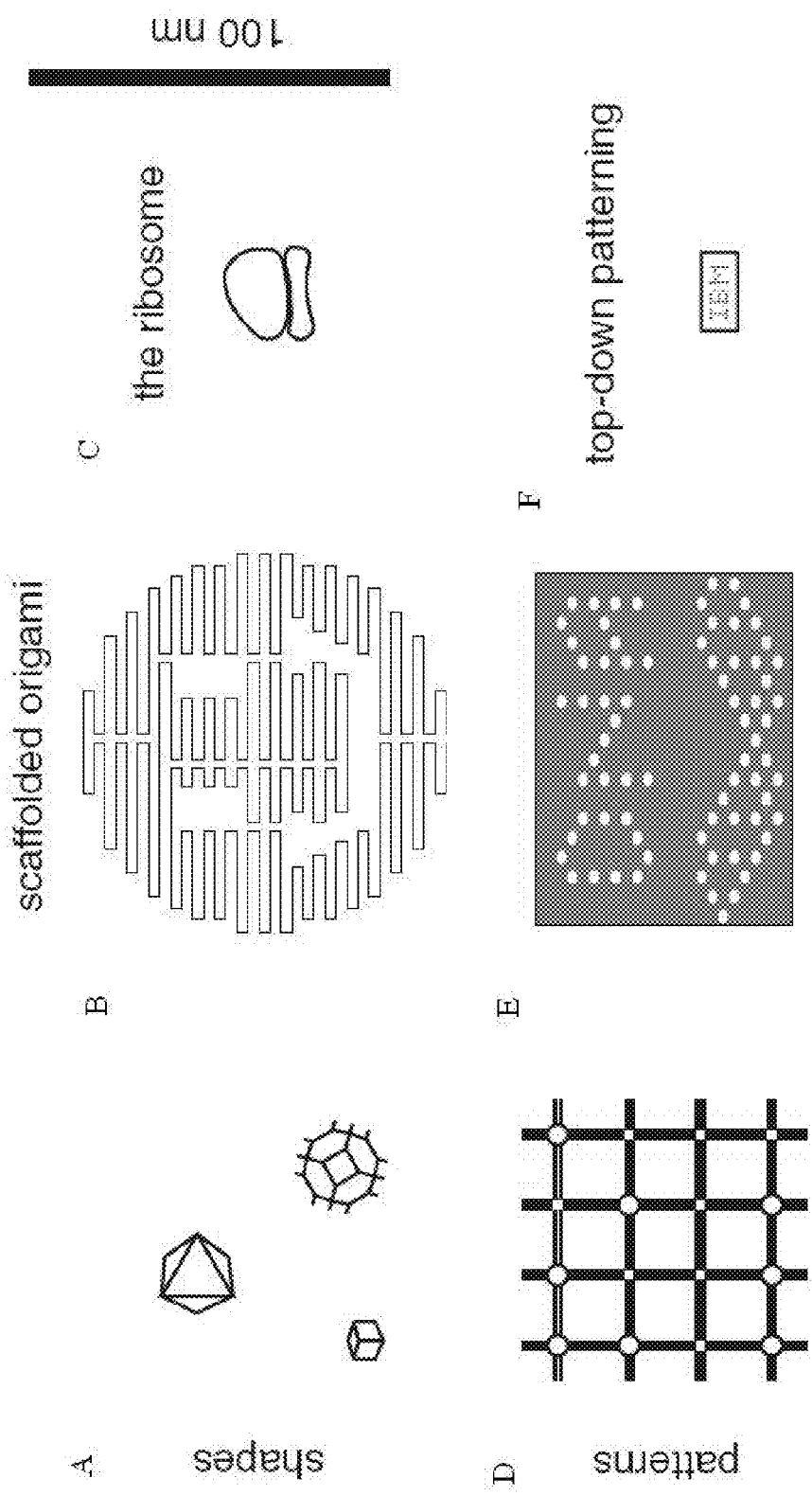
FIG. 6A-F shows a comparison of a nucleic acid origami structure of the invention to other nanostructures. (A) prior structures designed by linking individual shapes, difficult to perform with low yields. (B) A structure of the invention. (C) Natures ribosome. (D) A pattern structure. (E) A representation of a pixilated design. (F) The IBM logo generated by xenon atoms with an STM tip.

FIG. 6 compares the shapes and patterns now accessible by scaffolded nucleic acid origami based upon the methods and compositions of the invention to previously self-assembled DNA nanostructures, as well as to Nature's ribosome (which translates RNA messages into protein) and one of humankind's smallest written patterns. A few important differences include (a) the number of pixels available to scaffolded nucleic acid origami exceeds that previously demonstrated by more than a factor of 10, (b) the scale of the patterns formed by scaffolded nucleic acid origami is only 5× larger than that achieved by IBM scientists when they wrote their logo using xenon atoms with an STM tip, (c) fifty billion copies of the pattern are created at once in a single drop of water via scaffolded nucleic acid origami whereas only 1 copy can be created at a time using STM or AFM and (d) the molecular weight of scaffolded nucleic acid origami exceeds that of the ribosome-one can now assemble structures whose size and complexity rival that of Nature's most complex self-assembled machines.

The invention opens the door to a number of practical applications, for example, using scaffolded nucleic acid origami as templates for nanoscale circuits. Indeed, scaffolded nucleic acid origami may be viewed as a 'nanobreadboard' to which diverse components can be added. The nucleic acid nanostructures of the invention can be thought of as an analog of a breadboard in conventional electronics (a blank circuit board with a 2D array of holes to which a diverse set of components may be plugged-in and wired-up). The nucleic acid nanostructures of the invention can serve as template for the generation of components such as electronic switches or optical devices made from a large variety of materials (small molecules, silicon nanowires, gold nanocrystals, semiconductor quantum dots, and the like). For example, quantum dots to small organic molecules to proteins can be added. For example, the invention demonstrates that nucleic acid hairpins may be applied to an origami structure to create a pixilated composition by varying the height (thickness) of nucleic acids above a horizontal plane.

One type of circuit that may be possible to create in this way would be the optical analog of a radio frequency identity tag (RFID). The idea is that light could be used as the input to optical elements on a DNA origami (which might be flourophores or quantum dots) (see, e.g., FIG. 7). Information would then be processed by a circuit (composed of small molecule switches, gold nanoparticles, flourophores or quantum dots). The processed information (the ID of the tag or other output) would then be output optically (again by flourophores or quantum dots).

Using the methods of the invention, a number of nanostructures have been generated. As described in further detail below, the nanostructures comprise polynucleotide strands in various shapes. For example, different 100 nanometer two dimensional shapes have been demonstrated: a square, a rectangle, a 5-pointed star, two types of triangles, a disk with 3 holes in it, a map of the western hemisphere, the letters "DNA", a hexagonal "snowflake" pattern have been put on a rectangle and the numbers 1, 2 and 3 have been put on the arms of a triangle. Clearly the pattern that may be used is arbitrary. Details of the generation of both shapes and the overlayed patterns is disclosed herein. The shapes do not have to be solid, the scaffold strand can wind around the holes. The method can be applied to three dimensional shapes as well. The method can be used, for example, to generate 3D shapes such as cages, boxes and the like that can be used to restrain, hold, or capture a biological reactant. One biomedical application comprises the construction of cages that would sequester enzymes until they were ready for use in turning other proteins on or off. In one embodiment, the nucleic acid cage would have a lid or gate that could be actuated (open or closed) by the introduction of additional olignucleotides which would allow the reversible release or encapsulation of the biological agent.

In the examples, discussed below, DNA shapes are flat, uniform shapes. An arbitrary pattern of bumps or chemical functional groups can be added to form varied structures. Think of each helper strand in the above method as a black pixel, a "dot" in an image. Then the normal shapes can be thought of as an 'all black' version of the shape. To put a pattern, say 'X', of white pixels on the shape, one places the patterns on top of the design for the shape. Wherever a white pixel lies on top of a helper strand, one designs and synthesizes a new version of the helper strand that is modified to have a bump (e.g. hairpin of DNA) or chemical group of interest. One then just mixes together old helper strands for all the positions one wants to be black, and new helper strands for each position one wants to be white. The strands are heated and cooled as normal.

More generally, it is possible to make all $2^N$ possible patterns of N binary pixels by synthesizing just $2^N$ strands ahead of time. In the examples discussed below, origami typically have 216 pixels. This means that by combining a desired subset of 216 unlabelled "normal" staples with the complementary subset of 216 chemically functionalized "labeled" strands, any of $2^{216}$ or $10^{65}$ possible binary patterns can be made. The same procedure could be used to create patterns with a greater number of possible chemical groups at each pixel. For example, if 3 distinct sets of 216 helper strands each with a different chemical functional group were synthesized, then any of $3^{216}$ patterns would be immediately and quickly synthesizable.

Once shapes have been made, they can be joined together to form larger shapes. For example, 6 triangles can be joined together to make a hexagon. Or the triangles can be joined together to form a periodic lattice of triangles. Joining is accomplished by making simple changes to the helper strands so that one helper strand binds to two different copies of the shape. In one aspect, helper strands along on half of the edge of a shape are extended with single-stranded regions and helper strands along the other half of the edge of the shape are shortened to leave single stranded sections on the scaffold. The extended helper strands bind the single-stranded sections of the scaffold and join edges together.

As described in more detail herein, the scaffolded nucleic acid origami of the invention can be adapted to create more complex or larger structures. For example, the design of three dimensional structures is accessible using a straightforward adaptation of the raster fill method provided here. If non-repetitive scaffolds of megabase length can be prepared, micrometer-size origami with 20,000 features may be possible. In some aspect, the invention contemplates the combination of scaffolded nucleic acid origami of the invention with hierarchical self assembly, algorithmic self-assembly, or top-down fabrication techniques.

The scaffolded nucleic acid origami of the invention has application to the creation of a 'nanobreadboard', to which diverse components could be added. The attachment of proteins, for example, might allow novel biological experiments aimed at modeling complex protein assemblies and examining the effects of spatial organization, whereas molecular electronic or plasmonic circuits might be created by attaching nanowires or gold nanoparticles. These ideas suggest that scaffolded nucleic acid origami could find use in fields as diverse as molecular biology and device physics.

The shapes and patterns made from the nucleic acids can be used as templates for other materials to create interesting devices. For example, the pattern for a nanoscale circuit can be created based upon a nucleic acid pattern. Metal particles (for example, gold nanoparticles) may be attached to the pattern and annealed (e.g., to form wires) or closely associated to form a conductive coupling. Metal nanoparticles such as gold nanoparticles may also be used as optical devices through plasmonic couplings. The addition of other optical devices is possible, for example, fluorescent semiconductor quantum dots may be attached to the pattern. If optical devices are desired, semiconductive quantum dots may be attached to the pattern. Because the method is so versatile and simple the formation of any number of nanoscale structures can be generated by first forming a nucleic acid pattern using the methods of the invention. The pattern may then be further modified to form the desired nanoscale device.

DNA origami can be used to place protein molecules in particular patterns to study how they interact or to form nano- or micro-factories comprising proteins operably linked so as to function as assembly lines.

The invention provides a process for making nanoscale arrays. In one aspect, the arrays have a predetermined organization. The arrays comprise a polynucleotide organized in a desired shape, location, or structure (e.g., 2-Dimensional or 3-Dimensional). The array can further comprise nanostructure materials including metal, alloy, semiconductor and/or magnetic nanostructures. An "array" can be any arrangement such a nanostructure that is useful for forming electronic devices. Three primary examples of uses for such arrays are (1) electronic circuits, (2) arrangements of computer memory elements, both of which can be in one or several planes, and (3) sensors.

Nucleic acid origami nanostructures can be used to arrange nanoscale particles into patterns or systems. For example, a nanoscale particle has a radius on the order of about one nanometer. Nanoparticles can be linked to the helper strands and thus to the nucleic acid origami structure using techniques known in the art. The nanoparticles, so arranged by the nucleic acid origami template, can be used to generate electrical/optical devices/circuits or to facilitate measurement of various analytes using fluorescence, surface plasmon resonance (SPR) or Raman spectroscopy. The polynucleotide scaffolds of the invention provide a suitable substrate to provide electronic devices that operate at or about room temperature.

In one aspect, the nanostructure material (e.g., a metal, alloy, semiconductor and/or magnetic material) are bonded to polynucleotide scaffolds to organize the nanostructures into nanodevices, circuits and the like. "Polynucleotide scaffolds" comprise nucleic acid or nucleic acid analog polymers that are placed on a substrate in predetermined patterns, such as linear bridges between electrodes, and to which nanostructures can be bonded to provide organized arrays.

In one aspect, a method for forming arrays of metal, alloy, semiconductor and/or magnetic materials involves placing a polynucleotide scaffold on a substrate, in, for example, a predetermined pattern. Arrays are formed by contacting the scaffold with plural, monodispersed (nanostructures of substantially the same size) nanostructure-stabilized inorganic conductors such as a metal, alloy, semiconductor and/or magnetic nanostructures that couple to the polynucleotide scaffold. Examples of inorganic conductors that can be coupled to the polynucleotide structure include, for example, metals and metal alloys (Ag, Au, Cu, Pt, AuCu alloy, and the like), highly doped semiconductors (Si, GaAs, InP, $MOS_2$, $TiO_2$, and the like), conductive metal oxides ($In_2O_3$, $SnO_2$, $Na_2Pt_3O_4$, and the like), superconductors ($Yba_2Cu_3O_7$, $Ti_2Ba_2Ca_2Cu_3O_{10}$, and the like). If the materials are metal, then the metal may be selected from the group consisting of Ag, Au, Pt, Pd, alloys and mixtures thereof. In another aspect, carbon nanostructures may be linked to the polynucleotide scaffold.

In certain other embodiments, a conductive material that can be linked to a polynucleotide scaffold is a conductive particle, such as a colloidal nanoparticle. As used herein the term "nanoparticle" refers to a conductive particle having a diameter, length or width on the nanometer scale. Such nanoparticles are optionally stabilized with organic ligands.

Examples of colloidal nanoparticles for use in accordance with the disclosure are described in the literature. In this embodiment, the central core can be either non-conductive or conductive and comprises a ligand that is attached or linked to the central core making up the nanoparticle. These ligands (i.e., caps) can be polyhomo- or polyhetero-functionalized, thereby being suitable for detecting a variety of chemical analytes. The nanoparticles, i.e., clusters, can be stabilized by the attached ligands. In certain embodiments, the conducting components of the resistors are nanoparticles comprising a central core conducting element and an attached ligand optionally in a polymer matrix. In certain embodiments, the nanoparticles have a metal core. In other aspects, the core is made of a non-conductive material (e.g., an inorganic non-conductive material). In other embodiments, the ligand is a non-conductive material attached or linked to the metal core, wherein each metal core is in a matrix separated by non-conductive ligands. Typical metal cores include, but are not limited to, Au, Ag, Pt, Pd, Cu, Ni, AuCu and regions thereof.

Nanostructures (e.g., nanometallic particles) may be coupled to a polynucleotide scaffold by ligand exchange reactions. For example, each nanostructure, prior to contacting the polynucleotide scaffold, can comprise exchangeable ligands bonded thereto. The ligand-exchange reactions involve exchanging functional groups of the scaffold for at least one of the exchangeable ligands of the nanostructure that is present prior to contacting the scaffold with the nanostructures. Examples of exchangeable ligands suitable for forming metal nanostructures in accordance with the invention may be selected from the group consisting of thiols, thioethers (e.g., sulfides), thioesters, disulfides, sulfur-containing heterocycles, amines, pyridines, phosphines, carboxylates, nitriles, hydroxyl-bearing compounds, such as alcohols, and mixtures thereof.

Nanostructures may also be coupled to the scaffold by electrostatic interactions between the nanostructure and the scaffold. For example, nanostructures may include ligands that possess a charge or charges, either positive or negative, that serve to attract the nanostructures to oppositely charged scaffolds. In one embodiment, the nanostructure includes ligands having at least one positive charge and the scaffold is a polynucleotide having plural negative charges along its phosphate backbone. In a more particular embodiment, the nanostructure includes ligands having quaternary ammonium groups. In another embodiment, the nanostructure includes ligands with at least one negative charge, such as ligands having carboxylate or sulfonate group(s).

Nanostructures may be coupled to a scaffold through hydrophobic interactions. In one embodiment, the nanostructure includes ligands with a portion that can intercalate into polynucleotide (e.g., DNA). For example, the portion that intercalates into the polynucleotide scaffold may be an anthraquinone. Other examples of suitable intercalating portions include planar cations such as acridine orange, ethidium, and proflavin. In some embodiments, the portion facilitates intercalation at particular, sequence-specific sites within a polynucleotide molecule. In other embodiments the nanostructures are coupled to a scaffold through covalent bonds between the ligands of the nanostructure and the scaffold comprising the intercalating agent.

In another aspect of the invention, micro- or nano-factories can be designed. By micro- or nano-factory is meant a series of two or more enzymes arranged in a specific order to facilitate the generation of a desired product. For example, carotenoid biosynthesis requires the use of various enzymes that typically are present throughout the cytoplasm of an organism. Thus, the production efficiency is limited by the diffusion of a first by-product to the location of a second enzyme to covert the by-product to a second product and the like. For examples, a biologist might use a polynucleotide nano-scaffold of the invention to take proteins which normally occur separately in nature, and organize them into a multi-enzyme factory that hands a chemical by-product from one enzyme to the next in the manner of an assembly line.

Scaffolded nucleic acid origami may serve as a 2D or 3D scaffold for multi-enzyme factories. FIG. 7 shows an example. Three proteins, A, B, and C have been attached to a scaffolded nucleic acid origami in an arrangement so that they can act on three chemical monomers (say green stars, blue squares, and red hexagons, respectively for proteins A, B, and C) and polymerize them into long chains. The positions of the proteins A, B, and C dictate the order of the monomers in the final polymer. For example, when the proteins are arranged in a clockwise fashion A, B, and C, then the resulting polymer has repeating monomers in the order blue square/red hexagon/green star but when the proteins are arranged in a counterclockwise fashion then the resulting polymer has repeating monomers in the order blue square/green star/red hexagon.

Typical protein factories that might be built in this way might be based on proteins for making small peptides (linear or cyclic peptides), small carbohydrate molecules (oligosaccharides and other glycans), or proteins for doing sequential phosphorylation of other proteins (proteins in a kinase cascade).

The invention also provides compositions that are useful, for example, for forming metal, alloy, semiconductor and/or magnetic nanostructure arrays. In a particular embodiment, the composition comprises monodispersed, ligand-stabilized Au metal nanostructures coupled to a polynucleotide origami structure. In some embodiments, the metal nanostructures linked to the polynucleotide scaffold have metal-nanostructure radii of from about 0.4 nm to about 1.8 nm, such as from about 0.4 nm to about 1.0 nm.

The invention further provides an electronic device that operates at or about room temperature based on the Coulomb blockade effect. Such electronic devices include a first nanostructure (e.g., a nanostructure comprising a metal nanostructure core having a radius of between about 0.4 nm and about 1.8 nm) and a second such nanostructure. The nanostructures are physically spaced apart from each other at a distance of less than about 5 nm by coupling the nanostructures to a polynucleotide scaffold, so that the physical separation between the nanostructures is maintained. Electronic devices according to the invention may also include pairs of polynucleotide scaffolds, each with coupled nanostructures, arranged so that the scaffolds intersect to provide electric circuit elements, such as single-electron transistors and electron turnstiles. Such elements may be useful as components of chemical sensors or ultrasensitive electrometers. Because of their unique architecture, electronic devices according to the invention exhibit a linear increase in the number of electrons passing between pairs of nanostructures as the potential difference between the two nanostructures is increased above a threshold value.

In yet another embodiment, the invention provides the ability to generated nano-barcodes. For example, the barcodes comprise a polynucleotide scaffold generated by the methods of the invention. Oligonucleotides helper strands or helper strands and a plurality of additional oligonucleotides can be hybridized to the polynucleotide scaffold to generated a labeled scaffold. The label may comprise one or more "raised" structures thus generating a detectable change in the polynucleotide scaffold. Alternatively, the oligonucleotide can comprise one or more tag moieties. Various methods for producing tagged oligonucleotides are well known in the art. The barcode is formed by hybridization of a series of tagged oligonucleotides to the polynucleotide scaffold. Alternatively, the oligonucleotide can comprise an aptamer sequence that can bind to proteins, peptides or other target biomolecules.

Barcodes may be detected using any modality known in the art. For example, AFM and fluorescence spectroscopy may be used to detect a barcode. Various fluorescent dyes and moieties are known and can be attached to an oligonucleotide or other composition to be bound by the polynucleotide scaffold. In one aspect, intercalating agents can be linked to a fluorescent molecule. The amount and properties of the dyes in a barcode will determine the fluorescence emission profile of the barcode. For a given barcode composition, signals may also be affected by quenching and resonance energy transfer techniques.

Raman spectroscopy may be used to detect a barcode. Various nanoparticles with different geometries provides specific spectroscopic signals. Thus, different Raman tags can be attached to a barcode for detection by known Raman spectroscopy including surface enhanced Raman spectroscopy. In addition to attached Raman tags (e.g., gold nanoparticles), the polynucleotide scaffold itself may emit a Raman spectrum. For example, different base compositions of a nucleic acid produce different Raman signals.

The invention also provides gene-chip applications. "Gene chips" or hybridization arrays are used to measure the transcriptional state of a cell, that is, to determine which genes in a cell are turned on or off. For each gene that is turned on in a cell, a messenger RNA is produced. The presence of such a messenger RNA (mRNA) in a population of cells can be detected by lysing the cells, turning the messenger RNA into a complementary DNA (by reverse transcription) and binding the products to a 2D hybridization array of DNAs that are specific for the mRNA of interest. The hybridization array is often read-out with a fluorescent microscope. For each gene that is "turned on" in a population of cells, a particular spot on the hybridization array will "light up". Three cells in a population with a variety of mRNAs (colored bars) are lysed and their contents hybridized to a 2D array that allows readout of which mRNAs are expressed.

Because the mRNAs measured in this manner is derived from a population of cells, information about correlations in gene expression in a single cell is lost. That is to say, in a population of cells, gene 1 may always be expressed with a gene 2 but other genes 3, 4, and 5 might be randomly expressed from cell to cell.

In the standard assay there is no way to tell that in all cells genes 1 and 2 are expressed but that genes 3, 4 and 5 are expressed only in certain sub-populations; this information is lost.

Scaffolded nucleic acid origami provides a way to get at this single-cell gene expression information. DNA or RNA origami can be created inside of the cells. Different positions on the origami would be designed to be specific for binding the mRNAs for different genes. Each position for a particular mRNA would thus be a pixel. The cells could be lysed and the individual origami could be read out by atomic force microscopy (AFM).

Each origami would represent the transcriptional state of a single cell and thus would preserve information about correlations (or non-correlations) of mRNAs occurring (and thus which genes were turned on) in single cells.

In addition, scaffolded nucleic acid origami may be useful for engineering the cytoskeleton of cells. This would allow scientists to engineer the shape or mechanical properties of cells. For example, a hexagonal "artificial centrosome" can be made from scaffolded nucleic acid origami (the hexagon) that can be created inside the cell (with an RNA scaffold and RNA staples transcribed inside the cell). This artificial centrosome can be used as a nucleus to initiate the growth of DNA, RNA, or protein filaments or nanotubes that would interact with the normal cytoskeleton of the cell, or the cell membrane, and influence the shape of the cell (e.g., the cell would take on the shape of a six-sided star).

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. Thus, the terms nucleoside, nucleotide, deoxynucleoside and deoxynucleotide generally include analogs such as those described herein.

Typically a nucleic acid will comprise phosphodiester bonds, however, nucleic acids may comprise a modified backbone comprising, for example, phosphoramide, phosphorothioate, phosphorodithioate, O-methylphophoroamidite linkages, and peptide nucleic acid backbones and linkages. Other analog nucleic acids include those with positive backbones; non-ionic backbones and non-ribose backbones. Nucleic acids containing one or more carbocyclic sugars are also included within the definition of nucleic acids. These modifications of the ribose-phosphate backbone may be done to facilitate the addition of electron transfer moieties, or to increase the stability and half-life of such molecules in solution. As will be appreciated by those in the art, all of these nucleic acid analogs may find use in the invention as helper strands or as part of a polynucleotide used to generate the nanostructure. In addition, mixtures of naturally occurring nucleic acids and analogs can be made.

Peptide nucleic acids (PNA) which includes peptide nucleic acid analogs can be used in the methods and compositions of the invention. Such peptide nucleic acids have increased stability. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration.

In some embodiments, a nanostructure of the invention comprising a polynucleotide may comprise 1 or more distinct polymeric nucleic acid structures (e.g., at least 20, at least 50, at least 100, or at least 1000 or more distinct nucleic acid molecules). The nucleic acids may be single stranded or double stranded, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, and the like. Such nucleic acids comprise nucleotides and nucleoside and nucleotide analogs, and modified nucleosides such as amino modified nucleosides. In addition, "nucleoside" includes non-naturally occurring analog.

As used herein a substrate or surface upon which a polynucleotide scaffold is generated can be any substrate or surface that does not result in the degradation of the underlying nucleic acid structure. Typically the substrate or surface will comprise a charge particular of the type of application and/or ligand to be used or attached to the scaffold. Examples of suitable substrates and surfaces include, but are not limited to, glass, mica, polystyrene, polypropylene, stainless steel, silicon and the like.

The surface/substrate used in the methods, compositions and systems of the invention can be made of any material suitable attaching polynucleotides (e.g., such as those used in DNA microarray technology). For example, the substrate can be a material that can be easily sterilized such as plastic or other artificial polymer material. Any number of materials can be used to form the substrate/surface, including, but not limited to, polyamides; polyesters; polystyrene; polypropylene; polyacrylates; polyvinyl compounds (e.g. polyvinylchloride); polycarbonate (PVC); polytetrafluoroethylene (PTFE); nitrocellulose; cotton; polyglycolic acid (PGA); cellulose; dextran; gelatin, glass, fluoropolymers, fluorinated ethylene propylene, polyvinylidene, polydimethylsiloxane, polystyrene, and silicon substrates (such as fused silica, polysilicon, or single silicon crystals), and the like. Also metals (gold, silver, titanium films) can be used.

A polynucleotide scaffold (e.g., DNA) self-assembles upon a surface to duplicate a nano-scale pattern made of complementary strands. Once deposited on a substrate, the nucleic acid origami structure may be used as a template or as a mask for further processing of the substrate, for example, to pattern electronic circuits. For example, scaffold molecules can be polymerized as a bridge between electrodes on a substrate.

The various techniques, methods, and aspects of the invention described herein can be implemented in part or in whole using computer-based systems and methods. Additionally, computer-based systems and methods can be used to augment or enhance the functionality described herein, increase the speed at which the methods can be performed, and provide additional features and aspects as a part of or in addition to those of the invention described elsewhere in this document. Various computer-based systems, methods and implementations in accordance with the above-described technology are presented below.

A processor-based system can include a main memory, such as random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage medium refers to a floppy disk, magnetic tape, optical disk, and the like, which is read by and written to by a removable storage drive. As will be appreciated, the removable storage medium can comprise computer software and/or data.

In alternative embodiments, the secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM or PROM) and associated socket, and other removable storage units and interfaces, which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, and the like. Software and data transferred via a communications interface are in the form of signals, which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

In this document, the terms "computer program medium" and "computer usable medium" are used to refer generally to media such as a removable storage device, a disk capable of installation in a disk drive, and signals on a channel. These computer program products are means for providing software or program instructions to a computer system.

Computer programs (also called computer control logic) are stored in main memory and/or secondary memory. Computer programs can also be received via a communications interface. Such computer programs, when executed, enable the computer system to perform the features of the invention as discussed herein. In particular, the computer programs, when executed, enable the processor to perform the features of the invention. Accordingly, such computer programs represent controllers of the computer system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

In another embodiment, the computer-based methods can be accessed or implemented over the World Wide Web by providing access via a Web Page to the methods of the invention. Accordingly, the Web Page is identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the invention to launch an application to, for example, perform an analysis according to the invention.

It will also be recognized the molecular biology techniques can be used to generate a scaffolded nucleic acid origami in vivo. Another aspect of the invention pertains to vectors, e.g., expression vectors, containing a nucleic acid encoding at least one (typically a plurality of distinct) helper/staple strands (or a portion thereof). Such helper/staple strands can be expressed in a host organism (e.g., cell) wherein they helper/staple strands interact with a separate endogenous scaffold strand or a separate heterologous scaffold strand (e.g., a scaffold strand present in a separate vector). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise oligonucleotide helper/staple strands and may include a polynucleotide scaffold strand such that a scaffolded nucleic acid origami is generated upon expression of the vector within the organism or cell. Typically the vector is in a form suitable for expression in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like.

The recombinant expression vectors of the invention can be designed for expression of at least one (typically a plurality of distinct) helper/staple strands in prokaryotic or eukaryotic cells, e.g., bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Another aspect of the invention pertains to living organisms (e.g., host cells) into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, At least one (typically a plurality of distinct) helper/staple strands protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the nucleic acid of interest. Typical selectable markers include those which confer resistance to drugs, such as G418, hygromycin and methotrexate. Nucleic acid encoding a selectable marker can be introduced into a host cell on the same vector as that encoding at least one (typically a plurality of distinct) helper/staple strands or can be introduced on a separate vector. Cells stably transfected with the introduced nucleic acid can be identified by drug selection (e.g., cells that have incorporated the selectable marker gene will survive, while the other cells die).

Although the invention has been generally described above, further aspects of the invention will be apparent from the specific disclosure that follows, which is exemplary and not limiting.

EXAMPLES

Figure 3:
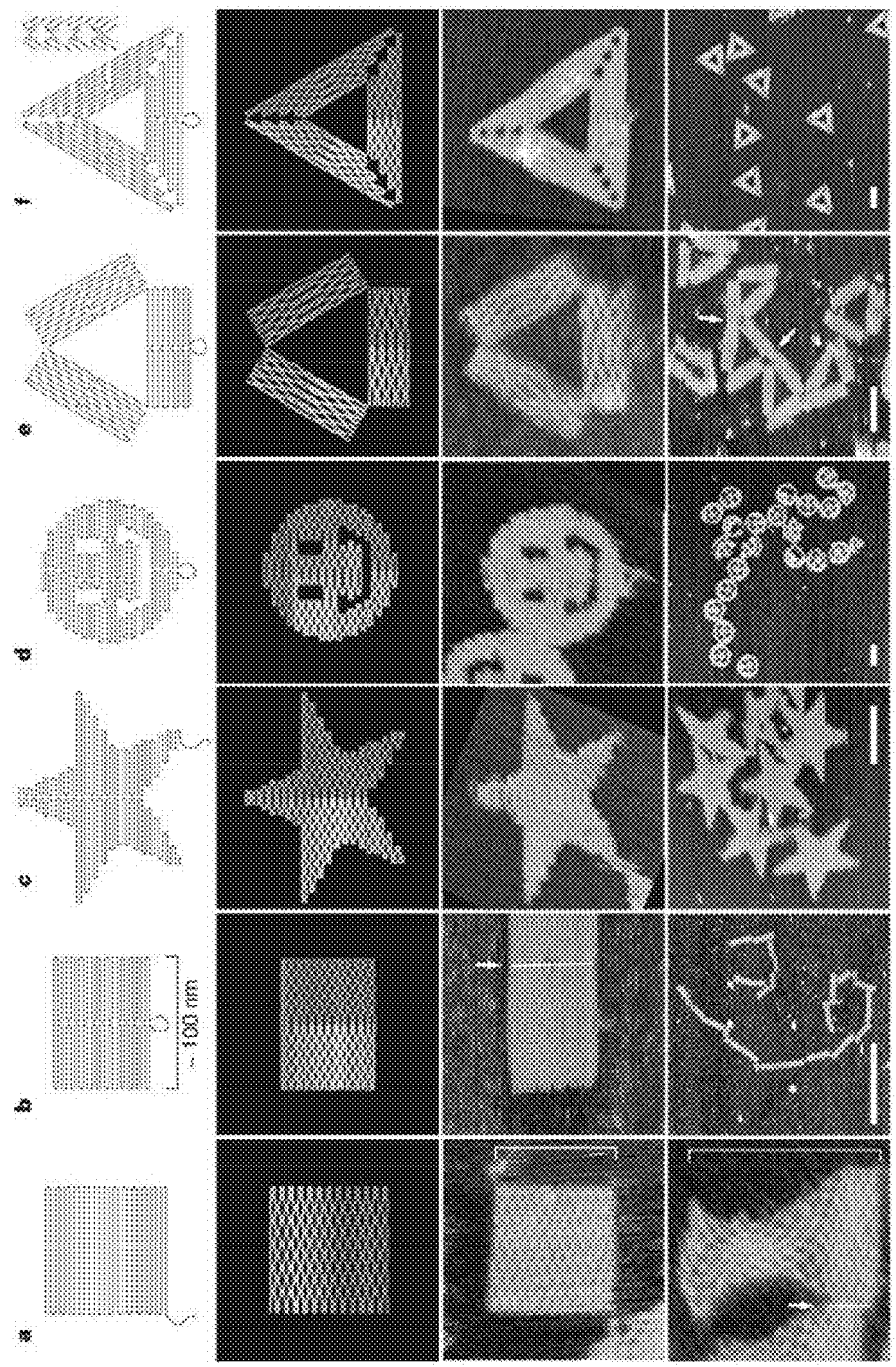
FIG. 3 shows arbitrary DNA shapes generated by the methods of the invention. Top row, folding paths. (A) square; (B) rectangle; (C) star; (D) disk with three holes; (E) triangle with rectangular domains; (F) sharp triangle with trapezoidal domains and bridges between them (lines in inset). Dangling curves and loops represent unfolded sequence. Second row from top, diagrams showing the bend of helices at crossovers (where helices touch) and away from crossovers (where helices bend apart). Bottom two rows, AFM images. White lines and arrows indicate blunt-end stacking. White brackets in (A) mark the height of an unstretched square and that of a square stretched vertically (by a factor of 1.5) into an hourglass. White features in (F) are hairpins; the triangle is labeled as in FIG. 4(K) but lies face down. All images and panels without scale bars are the same size, 165 nm±165 nm. Scale bars for lower AFM images: (B), 1 mm; (C-F), 100 nm.

To test the method of the invention, circular genomic DNA from the virus M13mp18 was chosen as the scaffold. Its naturally single-stranded 7,249-nt sequence was examined for secondary structure, and a hairpin with a 20-bp stem was found. Whether staples could bind at this hairpin was unknown, so a 73-nt region containing it was avoided. When a linear scaffold was required, M13mp18 was cut (in the 73-nt region) by digestion with BsrBI restriction enzyme. While 7,176 nt remained available for folding, most designs did not fold all 7,176 nt; short ($\leqq$25 nt) 'remainder strands' were added to complement unused sequence. In general, a 100-fold excess of 200-250 staple and remainder strands were mixed with scaffold and annealed from 95° C. to 20° C. in <2 h. When samples were deposited on mica, only folded DNA structures stuck to the surface while excess staples remained in solution; AFM imaging thus proceeded under buffer without prior purification. Six different folds were explored; FIG. 3 gives their folding paths and their predicted and experimentally observed DNA structures. Of the products imaged by AFM, a particular structure was considered qualitatively 'well-formed' if it had no defect (hole or indentation in the expected outline) greater than 15 nm in diameter.

For each fold the fraction of well-formed structures, as a percentage of all distinguishable structures in one or more AFM fields, was calculated as a rough estimate of yield. While some structures classified as well-formed had 15-nm defects, most had no defects greater than 10 nm in diameter. First, a simple 26-helix square was designed (FIG. 3a). The square had no vertical reversals in raster direction, required a linear scaffold, and used 2.5-turn crossover spacing. Most staples were 26-mers that bound each of two adjacent helices as in FIG. 2c, but via 13 bases rather than 8. The design was made assuming a 1.5-nm inter-helix gap; an aspect ratio of 1.05 (93.9 nm×89.5 nm) was expected. By AFM, 13% of structures were well-formed squares (out of S=45 observed structures) with aspect ratios from 1.00 to 1.07 and bore the expected pattern of crossovers (FIG. 3a, upper AFM image). Of the remaining structures, ~25% were rectangular fragments, and ~25% had an hourglass shape that showed a continuous deformation of the crossover lattice (FIG. 3a, lower AFM image). Sequential imaging documented the stretching of a square into an hourglass, suggesting that hour glasses were originally squares that stretched upon deposition or interaction with the AFM tip. No subsequent designs exhibited stretching. Other designs had either a tighter 1.5-turn spacing with 32-mer staples spanning three helical domains (FIG. 3b-d, f) or smaller domains that appeared to slide rather than stretch (FIG. 3e).

To test the formation of a bridged seam, a rectangle was designed (FIG. 3b) according to the scheme outlined in FIG. 2e using 1.5-turn crossover spacing, 32-mer staples and a circular scaffold. As seen in FIG. 3b, the central seam and associated pattern of crossovers was easily visualized (upper AFM image). Rectangles stacked along their vertical edges, often forming chains up to 5 mm long (lower AFM image). The yield of well-formed rectangles was high (90%, S=40), and so rectangles were used to answer basic questions concerning inter-helix gaps, base-stacking, defects and stoichiometry. AFM drift often distorts aspect ratios so that inter-helix gaps cannot be inferred from the aspect ratio of a single rectangle. A range of aspect ratios implied a gap size from 0.9 to 1.2 nm; later designs assume 1 nm. Whatever the exact value, it is consistent: aspect ratios were invariant along stacked chains with dozens of rectangles. Such stacking was almost completely abolished (when desired) by omitting staples along vertical edges.

On the other hand, stacking across the seam of an unbridged rectangle (as in FIG. 2c) kept 65% of structures (S=40) well-formed; the rest showed some degree of dislocation at the seam. Other defects, such as the intentional omission of single staples, could be visualized as 5-10-nm holes. However, sharp tips and high tapping amplitudes were required; repeated scanning created holes difficult to distinguish from holes due to missing strands. This effect also increased uncertainty when stoichiometry was varied. When staple excesses of approximately 100:1 and 9:1 were used, the frequencies of 5-10-nm holes (a few per rectangle) were indistinguishable. At 2:1, rectangles were similar; perhaps a greater fraction were malformed. At 1.5:1, rectangles formed but had holes up to ~10% of their area in size. At a 1:1 ratio, ~1% of structures were rectangular.

To demonstrate the creation of arbitrary shapes, a five-pointed star was designed with 1.5-turn spacing, 32-mer staples and a linear rather than circular scaffold (FIG. 3c). Designed assuming a 1.5-nm inter-helix gap (the work was carried out before the gap for 1.5-turn spacing was measured), the stars are somewhat squat (FIG. 3c, upper AFM image). Still, the stars show that the width of a shape may be approximated to within one DNA turn. Many of the structures observed were star fragments (FIG. 3c, lower AFM image), and only 11% (S=70) were well-formed. The low yield of stars (and squares, see above) may be due to strand breakage occurring during BsrBI digestion or subsequent steps to remove the enzyme; when untreated circular scaffold was folded into stars, 63% (S=43) were well formed.

To show that scaffolded nucleic acid origami need not be topological disks, and that scaffolds can be routed arbitrarily through shapes, a three-hole disk was designed (FIG. 3d). The holes in the shape were designed to take on the shape of a smiley face; this shows that precisely shaped holes can be created in a shape. Although the shape approximated is symmetric, the folding path is highly asymmetric and has five distinct seams. This shows that highly asymmetric paths and thus highly asymmetric shapes could be formed. Unlike the rectangles, which rarely break or fold, three-hole disks exhibit several characteristic deformations (FIG. 3d, lower AFM image); still, 70% (S=90) were well-formed.

DNA origami is not limited to the approximation of shapes by raster fill: some shapes can be created more exactly by combining distinct raster fill domains in non-parallel arrangements. FIG. 3e shows a triangle built from three separate, 2.5-turn spacing rectangular domains; only single covalent bonds along the scaffold hold the domains together. But the desired equiangular triangles (upper AFM image) were rarely observed (~1%, S=199). As seen in the lower AFM image, stacking caused rectangular domains of separate triangles to bind; this effect and the flexibility of the single-bond joints at the vertices may account for the ease with which these triangles deform. To solve these problems, 'sharp triangles', built from trapezoidal domains with 1.5-turn spacing, were designed (FIG. 3f). The slanted edges of the trapezoids meet at the triangle vertices and allow the addition of bridging staples along these interfaces. Sharp triangles remained separated and equiangular (FIG. 3f, lower AFM image); 88% were well-formed (S=78). Even when bridging staples at the vertices were not used, a large number of sharp triangles were well-formed (55%, S=22). These 'weakened' sharp triangles provided the most stringent test of the estimated inter-helix gap, because too high or low an estimate would have caused gaps or overlaps between trapezoids. Gaps of 10 nm occasionally appeared but overlaps were never observed, suggesting that 1 nm may be a slight underestimate of the inter-helix gap.

In addition to binding the DNA scaffold and holding it in shape, staple strands provide a means for decorating shapes with arbitrary patterns of binary pixels. Given a shape, the original set of staples is taken to represent binary '0's; a new set of labeled staples, one for each original staple, is used to represent binary '1's. Patterns are created by mixing appropriate subsets of these strands. In this way, any desired pattern can be made.

A variety of modifications, for example, can be made using biotin or fluorophores to serve as labels. For example, 'dumbbell hairpins' (FIG. 2d inset), designed to avoid dimerization at high concentration, were added to the middle of 32-mer staples at the position of merges made during design. Depending on the merge pattern, the resulting pixel pattern was either rectilinear, with adjacent columns of hairpins on alternate faces of the shape, or staggered and nearly hexagonally packed, with all hairpins on the same face. In AFM images labeled staples give greater height contrast (3 nm above the mica) than unlabelled staples (~1.5 nm), which results in a pattern of light '1' and dark '0' pixels. Several patterns (FIG. 4), each with ~200 pixels, illustrate the generality of this technique.

Yields of patterned origami were similar to those of unpatterned origami; for the pattern in FIG. 4a, 91% (S=85) of rectangles were well-formed. Because rectilinear patterns imaged poorly, only staggered patterns were examined quantitatively. Distances measured between pairs of '1' pixels in alternating columns (two pixel widths: 11.5±0.9 nm, mean±s.d., n=26) and adjacent rows (one pixel height: 6.6±0.5 nm, n=24) are consistent with the theoretically expected pixel size of 5.4 nm×6 nm. Most defects take the form of 'missing pixels'; that is, pixels that should image as '1's but image as '0's instead. 94% of '1' pixels (of 1,080 observed) were visualized. Whether missing pixels represent real defects or artifacts of imaging is unknown; sequential AFM images occasionally showed '1' pixels that later converted irreversibly to '0' pixels, suggesting tip-induced damage. Stoichiometric errors, synthetic errors, or unwanted secondary structure are not implicated for any particular strand, as the position of missing pixels appeared random (FIG. 4b, f and g).

Stacking of shapes along blunt-ended helices provides an uncontrolled mechanism for the creation of larger structures (FIG. 4b). Instead of removing staples on the edge of a rectangle to avoid stacking (as described previously), 4-T hairpin loops (four thymines in a row, FIG. 2e, inset) or 4-T tails can be added to edge staples (FIG. 4e, f); stacked chains of 3-5 rectangles still formed (FIG. 4g), but 30% of rectangles (S=319) occurred as monomers (FIG. 4i). Without hairpins, all rectangles occurred in aggregates (FIG. 4h).

Controlled combination of shapes was achieved by designing 'extended staples' that connected shapes along their edges. To create a binding interaction between two particular edges, extended staples were designed by merging and breaking normal staples along these edges. Starting with sharp triangles, this approach was used to create finite (hexagons; FIG. 4n, p, q) as well as periodic structures (triangular lattice; FIG. 4o, r-u).

Because the crossover sequences in the scaffolded nucleic acid origami demonstrated herein are determined by the M13mp18 sequence, and hundreds of crossover helper strands are used. Further, different crossover sequences show a varying tendency to assume one of two different stacked-X conformers, one of which is incompatible with the DNA origami's intended structure at every crossover. It is hoped that the juxtaposition of multiple crossovers in DNA origami inhibits both branch migrations and conformer isomerizations; isomerization or migration to an undesired form at one junction would tend to increase strain with adjacent junctions. A study of a symmetric antiparallel junctions juxtaposed with asymmetric antiparallel junctions has shown that the asymmetric junction can prevent adjacent symmetric junctions from branch migrating. But the same study showed that two symmetric antiparallel junctions juxtaposed next to each other can branch migrate. Thus it seems possible that several symmetric junctions near each other might conspire and migrate. Indeed it seems likely that some local rearrangements of junctions in origami happen; since they are likely to be smaller than a few nanometers, they cannot be observed by AFM. Eventually higher resolution structural information on DNA origami will determine if such isomerizations occur. Importantly, there is no reason why better characterized, well-behaved junction sequences should not be incorporated into DNA origami designs if it helps to create more precise structure. The incorporation of specific crossover sequences will require the use of a synthetic scaffold rather than a natural one, a practical inconvenience for very long scaffolds.

Figure 4:
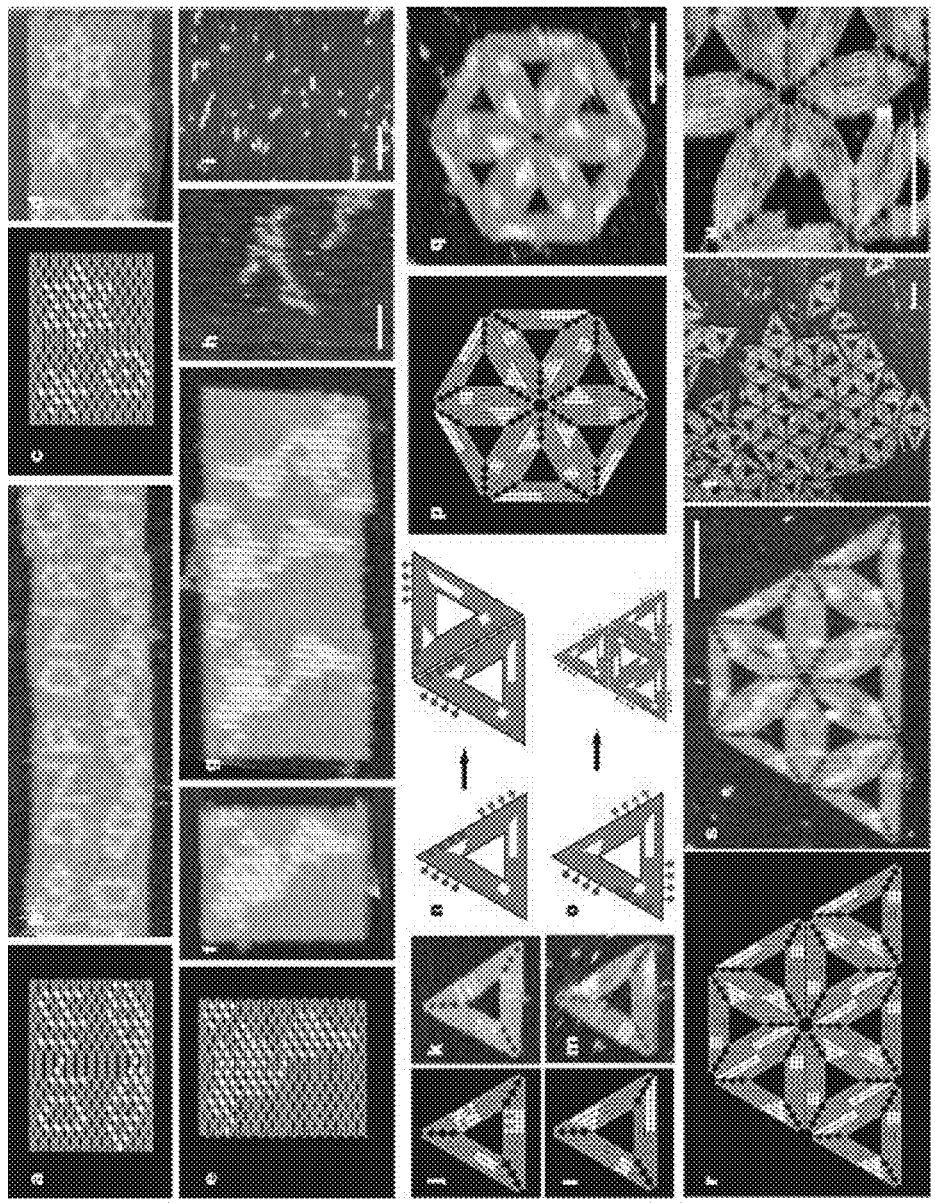
FIG. 4 shows patterning and combining DNA origami. (A) Model for a pattern representing DNA, rendered using hairpins on a rectangle (FIG. 3b). (B) AFM image. One pixilated DNA turn (~100 nm) is 30× the size of an actual DNA turn (~3.6 nm) and the helix appears continuous when rectangles stack appropriately. Letters are 30 nm high, only 6× larger than those written using STM; 50 billion copies rather than 1 were formed. (C-D) Model and AFM image, respectively, for a hexagonal pattern that highlights the nearly hexagonal pixel lattice used in (A)-(I). (E)-(I), map of the western hemisphere, scale $1:2 \times 10^{14}$, on a rectangle of different aspect ratio. Normally such rectangles aggregate (H), but 4-T loops or tails on edges (white lines in (E)) greatly decrease stacking (I). (J-M), Two labelings of the sharp triangle show that each edge may be distinguished. In J-U, pixels fall on a rectilinear lattice. (N-U) Combination of sharp triangles into hexagons (N, P, Q) or lattices (O, R-U). Diagrams (N, O) show positions at which staples are extended (protrusions) to match complementary single-stranded regions of the scaffold (holes). Models (P, R) permit comparison with data (Q, S). The largest lattice observed comprises only 30 triangles (t). (U) shows close association of triangles (and some breakage). (D) and (F) were stretched and sheared to correct for AFM drift. Scale bars: H, I, 1 mm; (Q, S-U) 100 nm.
Figure 5A:
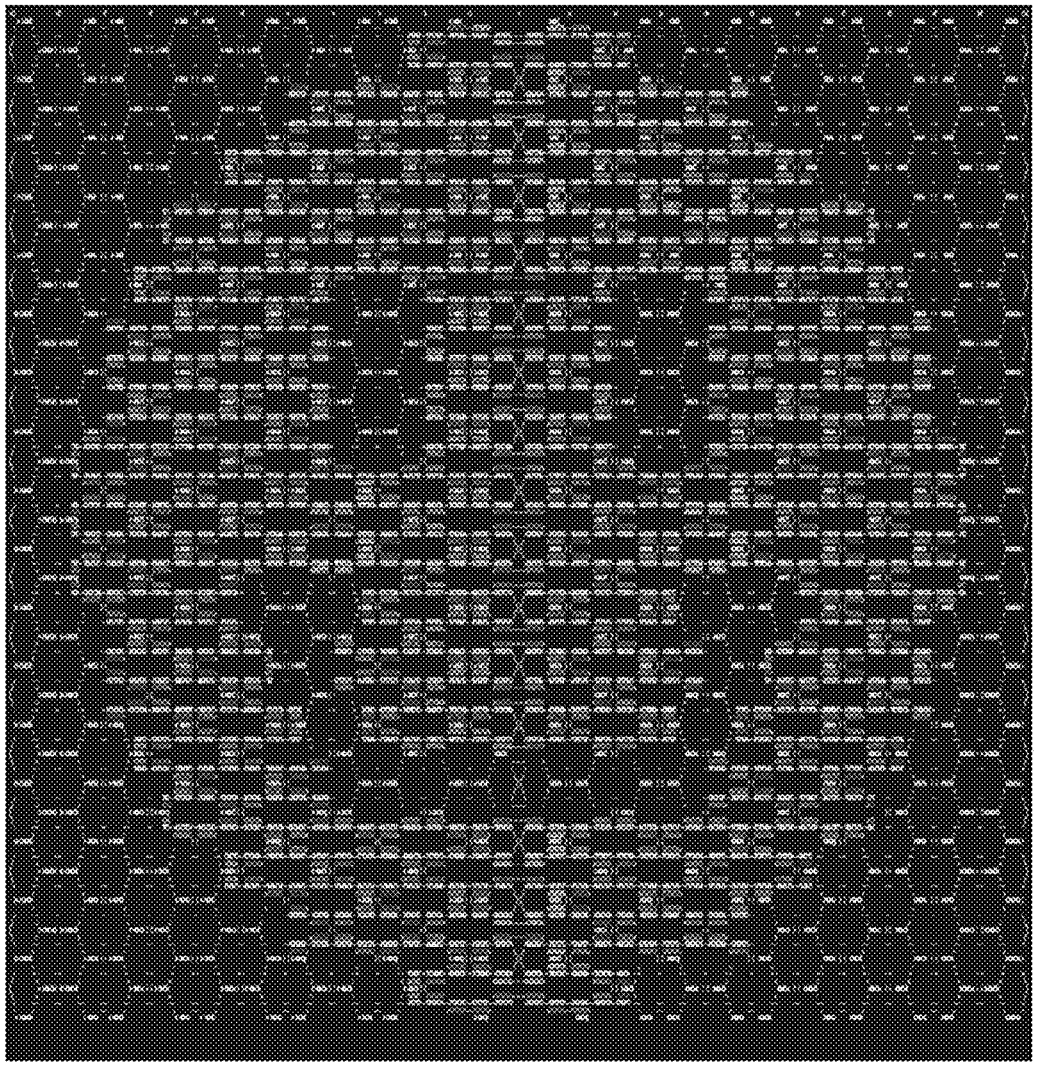
FIG. 5A-C shows (A) a smiley face origami and (B-C) related sequences. (B-C) show successive enlargements of a portion of the smiley face origami of (A) depicting the sequence (i.e., a partial scaffold sequence of M13mp18; SEQ ID NO:1) and related staple/helper strand sequences (SEQ ID NOs:2-23).
Figure 5B:
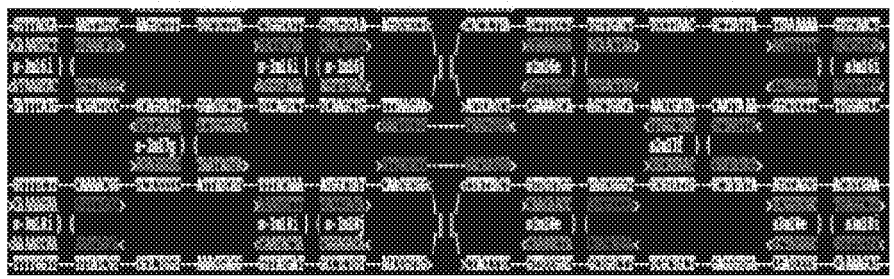
Figure 5C:
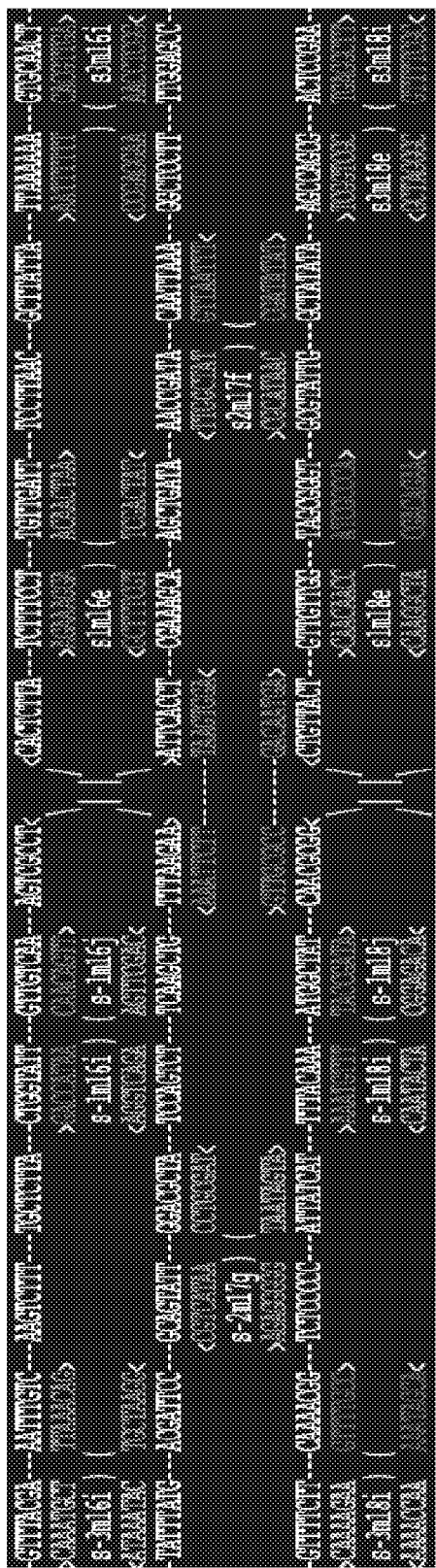

As an exemplary of the method of the invention, FIG. 4 provides ⅓ of a square origami design with helper and scaffold sequences explicitly written out for one specific scaffolded nucleic acid origami generated by the methods of the invention. The first test of the DNA origami method, before the creation of the full square, was the creation of the bottom ⅓ of the square (FIG. 4). Also, a circular M13mp18 scaffold was used rather than a linearized one, because the corners of the rectangle were close enough that the unfolded portion of the virus could easily bridge the corners without deforming the rectangle. No remainder strands were used on the ⅔ of the virus left unfolded. Apparently long, unfolded single-stranded sections of the scaffold do not adversely affect folding and remainder strands (on other designs) are probably unnecessary. ⅓ squares were observed singly or as dimers. Dimers always appear to be the result of stacking of ⅓ squares on the vertical edge away from the unfolded single scaffold. Thus the unfolded scaffold appeared to prevent stacking. Single-stranded scaffold takes on a 'cloud-like' appearance that varies from AFM image to AFM image. Coplanar helices in DNA nanostructures appear to bind mica cooperatively; the larger a DNA nanostructure, the more tightly it appears to bind mica. This trend is apparent in the mobility of DNA nanostructures deposited on mica and imaged by tapping mode AFM under buffer. Most of the structures described move infrequently during imaging, occasionally rotating by a few degrees or slipping by a few tens of nanometers (as judged by stationary structures around the mobile structure). The ⅓ squares, however, were more difficult to image because they often slipped, as shown in characteristic images.

Oligos were received from the manufacturer (Integrated DNA technologies) at a nominal concentration of 100 or 150 µm as determined by UV absorbance at 260 nm. To estimate the error in stoichiometry, the concentration of 10 helper strands were remeasured by UV absorbance upon receipt by diluting 4 µl of stock solution with 196 µl of distilled water. This modeled the type of pipetting errors that occurred in the experiments since typically 3-7 µl of each helper stock solution was used when helpers were mixed. (In a given experiment a fixed volume of each helper strand was used so no renormalization was performed.) Concentrations were calculated based on extinction coefficients calculated according to a nearest neighbor model. Assuming that the nearest neighbor model is correct, errors in absolute concentrations ranged from −5% to +13% and averaged +6% with a standard deviation of 6%.

This may have reflected a systematic difference between the manufacturer's and the laboratories spectrophotometers. Nevertheless, this means that errors in relative concentration had a range of roughly 20%, and thus estimated error in concentration of ~10% was calculated. The virus strand was similarly quantitated but variable volumes of it were used to achieve a desired concentration in the final experiment. Pipetted in small 1-2 µl volumes, its stoichiometry relative to the helper strands is assumed to be similarly ~10%.

To test the ability of atomic force microscopy to observe defects in origami, rectangles were prepared with three helper strands intentionally omitted. In low resolution images of the lattices, no defects were observed; the majority of AFM tips did not provide resolution that allowed imaging of the defects. With high resolution tips, 'holes' at the position of the missing strands were observed, although not all rectangles showed all three holes immediately upon imaging; it sometimes took repeated imaging for holes to appear, as if the AFM tip were enlarging the defect.

Unbridged seams in scaffolded origamis are those held together only by stacking interactions. Large dislocations at unbridged seams are also common.

Stacking interactions based on blunt-ended helices can be quite strong; rectangles which have many parallel blunt ends along their left and right edges stack so strongly that they may form long chains over 5 microns in length. While, as deposited on mica, an offset occurs every few rectangles along such a chain, to avoid aggregation based on stacking interactions, several methods can be employed. First, the helper strands along the edges of a shape may be simply left out, and the scaffold left unstructured along these edges.

Use of circular scaffold with stars appears to give better results than with linear scaffold. Fewer structures appear to be fragments of stars. However, it is difficult to tell whether the lower two points of the star, which the circular scaffold bridges, are well-formed. The circular scaffold that bridges the two lower points is easily visualized, however, as a single, somewhat diffuse, arc. The fact that circular scaffold appeared to give better results may be attributed to the high purity of the circular scaffolds. After linearization, the quality of linear scaffold, in terms of the percentage of strands that were full length, was not assessed and a large percentage of the strands may have not been full length.

While all viruses labeled M13mp18 are supposed to have identical sequences, in practice this does not appear to be the case. The originally deposited sequence for M13mp18 in Genbank (accession X02513, 7249 bases long, incorporated herein by reference (SEQ ID NO:1) appears to have an error that was corrected by adding a 'T' at position 900 (accession M77815, 7250 bases long). Amersham Biosciences gives the sequence of M13mp18 as a 7249 sequence that differs from X02513 by a pair of compensatory frame shifts (bounding the region from 977 to 1556) and 3 point mutations outside of the frame shift. New England Biolabs gives a 7249 sequence for their clone (resequenced in 2002) that differs from the Amersham sequence by a pair of compensatory frame shifts (bounding the region 900-977) and 23 point mutations outside of the frame shift. The helper strands given in this paper were created using the New England Biolab's sequence and all experiments save those described here were performed with New England Biolab's M13mp18.

To test whether small differences in sequence could be detected by AFM, helpers for the rectangle were used to fold a sample of M13mp18 from Bayou Biolabs (which reports that their sequence is the same as that of Amersham, although it has not been recently resequenced). Thus the helper strands should have had mismatches with the scaffold at 23 positions and a 78 base section should have been shifted by 1 base with respect to the scaffold. Qualitatively, no differences were observed between rectangles created with Bayou Biolabs M13mp18 DNA and New England Biolabs M13mp18 DNA.

To label a DNA nanostructure, DNA hairpins are often added to increase the height of the nanostructure at a desired location. DNA hairpins have a tendence to dimerize, and, at the high concentrations at which they occur (up to 40 µM if all positions were labeled by the same hairpin) might inhibit formation of the shapes. Thus a new type of hairpin, a dumbbell hairpin was designed (FIG. 1D) that, in order to dimerize, must form a presumably strained pseudo-knotted structure.

Because the set of '0' strands and set of '1' strands (bearing dumbbell hairpins) are complementary, and '0' and '1' strands are stored in characteristic positions of matched 96 well plates, two complementary pipette tip boxes are easily constructed, one for selecting the '0' strands and the other for selecting '1' strands. This is accomplished by taking a full tip box, and, for each position of a desired '1', moving that tip to the same position in an empty tip box. The full tip box becomes a box for selecting the '0' strands, and the empty tip box becomes a box for selecting the '1' strands. A multichannel pipettor or robotic workstation can then be used to apply the tip boxes to the 96 well plates. The pipettor gets a tip if and only if the corresponding position in the tip box has a tip, and thus performs only the desired pipetting operations.

To give sharp triangles specific binding interactions, helper strands along their edges were cut and pasted to yield two new types of helper strands: (1) extended helper strands that projected 8 bases off of the edge of the triangle (2) truncated helper strands that left an 8 base section of the virus single-stranded. Given a sharp triangle as drawn in the design (with a particular face of the triangle facing up out of the page), extended helper strands were positioned on the right-hand half of the sharp triangle's edge and truncated helper strands were positioned on the left-hand half the sharp triangles edge. In this way, whenever the edges of two triangles met (with the faces of the triangle pointing in the same direction) the position of extended helper strands on one edge matched up with the position of the truncated helper strands on the other edge (and vice versa). If the extended helper strands matched the single-stranded portions of the scaffold, then they could bind.

The formation temperature of sharp triangles relative to the formation of inter-triangle bonds is probably important to the correct composition of triangles. Ideally, over the course of annealing, sharp triangles would form completely at a high temperature, and then only at a much lower temperature would weak inter-triangle bonds be strong enough to bring triangles together. If the bonds between triangles are too strong, then they will form at a temperature near that at which the sharp triangles themselves form and the sharp triangles may still be partially melted, disordered and sloppy. This would seem to result in poorly formed structures.

The strength of inter-triangle interactions can be tuned by the number of extended helper strands that are used. Variations in which 2, 4, 8, and 16 helper strand bridges should have formed between sharp triangle edges were performed. Hexagons and lattices formed with 4 and 8 helper strand bridges between edges but not for 2 and 16 helper strands. The experiments suggest that 2 bridges are too weak, and 16 bridges are too strong, for proper composition of triangles. It is possible that on average 2 acceptor sites per edge were filled with excess extended helper strands. If this were true then it would explain why in 2-bridge experiments, few triangles bound each other. Further, the 16-bridge experiments are not really comparable with the others. In the 16-bridge experiments, the acceptor (left side) of a sharp triangle is left almost completely single-stranded and sloppy because 8 truncated helper strands occur in a single row. This is in sharp contrast to the 4 and 8 bridge experiments in which truncated helper strands alternate with normal helper strands on the acceptor side of the edge; the normal helper strands potentially make the edge more rigid.

Repetition of sequences (and their complements) in the scaffold and helper strands may cause them to have undesired binding to each other or to themselves. How much repetition can be tolerated is an interesting question. Understanding such limits will require solving difficult combinatorial and thermodynamic problems. Below are examples of secondary structure and other undesired binding interactions in M13mp18 and the helper strands, structure that was not difficult to overcome. For its length and base composition, M13mp18 is not special in this regard it is not a particularly "lucky" sequence with little secondary structure. To get a feeling for M13mp18 secondary structure, Michael Zuker's DNA Mfold, available on the Internet, was used to obtain predicted foldings for 6000 base sections of M13mp18, as well as predicted foldings of 6000 base random sequences of similar base composition. All folds were computed at 20° C., 40 mM Na+ and 12 mM Mg++. Rather than use the M13mp18 sequence reported in Genbank, the sequence by New England Biolabs (NEB) was used based upon the last time their M13mp18 clone was resequenced, (F. J. Stewart, NEB, May. 28, 2002).

Lowest energy folds for seven 6000 base segments of M13mp18 (using a sliding window, starting at n=1; 1001, 2001, 3001, 4001, 5001, 6001 and 7001) were obtained. The strongest structure (n=4001, −1003 kcal/mole) and weakest structure (n=6001, −904 kcal/mole) were identified. Strong secondary structure was noticed around base 5500. This structure, a series of several strong hairpins, is well-known structure of biological significance and occurs in the intergenic region (5500-6000) of M13. Of particular interest is a strong 20 base hairpin. To get a quantitative measure of the predicted secondary structure the free energies of folding were averaged (for the lowest energy structures). For the seven sections examined the average is ~965±37 kcal/mole. The large variation in energy is due to the fact that these 6000 base segments can be classed into two types; (1) those that span the intergenic region (n=1001, 2001, 3001, 4001, 5001) with its strong, biologically relevant secondary structure have an average energy of ~990±12 kcal/mole. Those that don't span the intergenic region completely (n=1, n=6001, n=7001) which have an average energy of ~924±24.

To evaluate whether M13mp18 has unusually strong or weak secondary structure, ten random 6000 base sequences were generated to have a base composition similar to M13mp18 (24.4% A 21.1% C 21.2% G 33.4% T, fixed at 1462 A's, 1266 C's, 1270 G's, 2002 T's). Visually it appears that M13mp18 has secondary structure similar to that of a random sequence of similar length. However, the average calculated energy for random sequences is significantly less than that for M13mp18, ~867±13 kcal/mol. Thus it seems that M13mp18 has somewhat stronger secondary structure than would be expected.

The secondary structure of M13 does appear to be less strong than that predicted for sequences of even base composition. For comparison, ten 6000 base sequences of composition A=G=C=T=1500 have an average calculated free energy of ~1080±21. To explore the strong effect that base composition has on secondary structure, two more examples were tested. For A=G=T=2000 and C=0 the predicted average energy is ~157±13. And for A=C=T=2000 and G=0 the predicted average energy is ~93±6. In the event that secondary structure becomes a limiting factor in the creation of DNA origami, such skewed base compositions might be used but at the cost of specificity in helper-scafiold binding. Of all the potential secondary structure that the M13mp18 sequence has, only the [A] loop was deemed worrisome enough to be avoided. Mfold predicts the structure of loop [A] as a hairpin, (20 nt stem, 4 G-T mispairs, ~G=−14.4 kcal/mole) at positions 5515-5557 of SEQ ID NO:1. The sequence at these positions is: GGCGGGTGTGGTGGTTACGCGCAGCGT-GACCGCTACACTTGCC. In designing DNA origami, this sequence was avoided (73 base section (5515-5587 of SEQ ID NO:1)GGCGGGTGTGGTGGTTACGCGCAGCGT-GACCGCTACACTTGCCAGCG CCCTAGCGCCCGCTC-CTTTCGCTTTC). This allowed linearization of M13mp18 by incubating with the complement of bases (5558-5587) GAAAGCGAAAGGAGCGGGCGCTAGGGCGCT and cutting with BsrBI between positions 5573 and 5574. (BsrBI has recognition sequence, CCGCTC at 5571-5576 of SEQ ID NO:1; it leaves a blunt end between bases 3 and 4 above).

Other less strong but well known secondary structure in the scaffold did not seem to cause problems. For example, the hairpin [C] GGGTGATGGTTCACGTAGTGGGC-CATCGCCC has a 14 base-pair stem. Occurring at bases 5704-5734 of SEQ ID NO:1, this sequence is 116 nucleotides into the origami structures. It occurs, for example in the rectangle on the bottom edge of the lower left corner, a position that suffers no apparent defects. The helper strands themselves may have unintended secondary structure or binding interactions. By concatenating the sequences of helper strands with 'NNNN' linkers between them and folding the resulting sequence with Mfold to find a couple potential bindings between different helper strands (with lengths of 10 and 11 nucleotides and having single G-T mispairs) as well as some secondary structure within single helper strands. For example, the rectangle helper strand r7t22e, GCCAACAGT-CACCTTGCTGAACCTGTTGGCAA (SEQ ID NO:24) can form an 8 base hairpin:

```
GCCAACAGTCACCTT\
|||||||
AACGGTTGTCCAAGTCG/
```

Such secondary structure would normally be considered unacceptable in a DNA nanostructure. Such scaffold and helper secondary structure might not cause problems for the formation of scaffold DNA origami. Consider any secondary structure that the scaffold might assume. It is unlikely that this secondary structure perfectly blocks the binding sites for all the helper strands that should bind its sequence. Thus helper strands may bind by partial matches at first (to gain a 'toe-hold'), and then participate in a branch migration that displaces the secondary structure. A longer region of complementarity between the helper and the scaffold stabilizes the helper-scaffold interaction over the scaffold secondary structure. The excess of helper strands may help drive this process. Another factor that may work against scaffold secondary structure is the role of helper strands as intramolecular bridges. Each successful addition of a helper strand organizes the scaffold for subsequent binding of adjacent helper strands and constrains the scaffold in a way that precludes a large set of undesired secondary structures. Thus one might expect the binding of helper strands to be highly cooperative. To see why intramolecular interactions may be important, consider cutting a scaffolded shape into a multi-stranded structure based on unique tiles (for which the minimum free energy state should be the scaffolded shape, just with more backbone nicks). For such a system the addition of a tile at any one position does not significantly constrain the global structure. Next consider the interactions of helper strands with themselves. Many strong complexes exist between them; none is a perfect match, however. The scaffold can displace such structure and gain a required helper strand. Now consider purity. A truncated helper strand might bind to the scaffold. However, because of the excess of helper strands, there exist many full length helper strands that can bind and displace the truncated strand. This means that only the purity of the scaffold matters; because the scaffold is derived from a biological source, it is very pure.

In a similar way, because helper strands do not bind to each other, the relative stoichiometry between the helper strands does not matter. With helper strands in excess over the scaffold, the remaining relevant concentration is the effective local concentration of scaffold in intramolecular events. Here the intramolecular nature of scaffold folding enforces a kind of equimolarity on any two sections of the scaffold that are brought together by a helper strand are by definition, equimolar. Again, such could not be said for the same sections if the scaffolded structure were cut into multi-stranded unique tiles.

This highlights a crucial difference between the scaffolded method shown here and DNA nanostructures. In the latter scheme the scaffold runs through every other helix; the structure is held together by interactions between multi-stranded tiles and so the helper strands must bind to each other. For such schemes precise equimolarity is likely important.

Given an estimate of the inter-helix gap it is easy to estimate the height of a DNA origami: the height is given (in nanometers) by height=2*(Number of helices)+(the interhelix gap)*(number of helices−1). It would appear, a priori, more difficult to estimate or design the width of a DNA origami. This is because the creation of an inter-helix gap appears to require that the DNA helices bend back and forth between the crossovers in which they participate. If one assumes that the contour length of a helix of DNA does not change as it bends and follows a curve, then the end to end distance of a DNA helix following such a curve must be shorter than the end to end distance of a straight helix of the same number of nucleotides. That is, to get a correct estimate for the width of an origami, one must take the bend into account. Exactly what curve is followed by the helix is probably affected by electrostatic repulsion between the DNA backbones, mechanics of DNA bending, the amount of supercoiling between crossovers, and detailed geometry of the junctions.

These factors can be ignored to get a very rough estimate of the change in width due to helix bending, close-packed versions of the 2.5 turn spacing and 1.5 turn spacing lattices were deformed by bending the helical domains between crossovers an amount appropriate to create the inter-helix gap (~10 degrees). The projection of these bent domains on the x-axis was then calculated and taken as the new width between crossover. The width between crossovers changed less than ~2% in both cases, because of the small angles involved. 32 nucleotides was used to cover 3 helical turns in the 1.5 turn spacing designs, the DNA in most designs is over twisted (relative to 10.5 bases/turn) by 1.5%. Thus it is possible that relaxation of supercoiling might have a compensatory effect (relative to the effect of bending) on the width of DNA origami. (On the other hand, 52 bases are used to cover 5 turns in the 2.5 turn spacing designs and they are 1% undertwisted, with respect to 10.5 bases/turn). It appears that the width of an origami can be estimated to within 2% without taking helix bending into account, merely be multiplying the number of bases in the widest helix by 0.34 nanometers.

A number of embodiments of the invention have been described. Nevertheless, it will be understood that various modifications may be made without departing from the spirit and scope of the invention. Accordingly, other embodiments are within the scope of the following claims.

What is claimed is:

1. A method for ex-vivo production of a non-naturally occurring nucleic acid nanostructure of arbitrary 2-D or 3-D shape comprising:
   a) selecting a desired shape for the nanostructure;
   b) providing a single stranded DNA polynucleotide scaffold having a known sequence;
   c) designing a folding path for said polynucleotide scaffold to form said desired shape;
   d) designing a plurality of single stranded oligonucleotide helper/staple strands to hold said polynucleotide scaffold based on said desired shape wherein said oligonucleotide helper/staple strands are at least partially complementary to said polynucleotide scaffold such that said oligonucleotide helper/staple strands anneal with said polynucleotide scaffold into a domain comprising a B-form DNA structural unit and wherein a subset of said oligonucleotide helper/staple strands have annealing sites that constrain crossovers and contact points between helices to form desired angles and desired shape and wherein a set of said oligonucleotide helper/staple strands form a loop between parallel strands of said polynucleotide scaffold;
   e) mixing said single-stranded polynucleotide scaffold with said plurality of oligonucleotide helper/staple strands to form a mixture; and
   f) producing said nanostructure by allowing said polynucleotide scaffold and said plurality of oligonucleotide helper/staple strands to anneal, wherein at least a subset of said oligonucleotide helper/staple strands bind said polynucleotide scaffold in two or more separate regions and bring these separate regions of said polynucleotide scaffold together to form a desired bend or angle in the polynucleotide scaffold producing parallel helices held together by a periodic pattern of crossovers spaced so that the distance between crossovers formed by two consecutive oligonucleotide helper/staple strands is an odd number of half turns apart.

2. The method of claim 1, wherein helices of the polynucleotide are parallel and these parallel helices are constrained by a helper/staple strand crossovers and separated by a gap of about 2 nanometers.

3. The method of claim 2, wherein two or more individual domains of the nanostructure are composed of parallel helices and the domains are non-parallel such that the domains have a defined angle between them.

4. The method of claim 2, wherein at least two planar domains of a structural unit have parallel helices constrained to be at 90 degrees to each other, forming a 3D structure, the helices of the first domain connected to the helices of the second domain by a set of crossovers that occur halfway between helper/staple strand crossovers of the first domain, an odd number of quarter turns from said crossovers.

5. The method of claim 1, wherein three adjacent parallel helices of a domain of the polynucleotide scaffold form an angle of 180 degrees and structural unit assumes a flat conformation.

6. The method of claim 1, wherein two or more individual domains of the structural unit are composed of parallel helices and the domains are non-parallel such that the domains have a defined angles between them.

7. The method of claim 6, wherein domains of the nanostructure are connected by the single covalent bond of the scaffold polynucleotide.

8. The method of claim 6, wherein domains of the nanostructure are connected by stacking interactions between blunt-ended helices.

9. The method of claim 6, wherein domains of the structural unit are connected by helper strands that bridge helices of one domain to helices of another domain.

10. The method of claim 1, wherein at least two domains of the polynucleotide scaffold have parallel helices that are held together by a pattern of crossovers spaced so that the distance between crossovers formed by the olignucleotide helper/staple strands is chosen according to the twist of the nucleic acid being used so that three adjacent parallel helices form an angle different than 180 degrees and the domain assumes a bent, corrugated or curved surface in 3D.

11. The method of claim 10, wherein the pattern is non-periodic.

12. The method of claim 1, wherein the oligonucleotide helper/staple strands are designed to fold the scaffold into a 2D or 3D polygonal network wherein the edges of the network are comprised of domains of at least two parallel helices.

13. The method of claim 1, wherein the polynucleotide scaffold and oligonucleotide helper/staple strands form a DNA:DNA duplex.

14. The method of claim 13, wherein a B-form of DNA is generated having a twist of about 10.5 base pairs per turn.

15. The method of claim 1, wherein the polynucleotide scaffold and oligonucleotide helper/staple strands form a RNA:DNA duplex or RNA:RNA duplex.

16. The method of claim 15, wherein an A-form of a duplex is generated having a twist of about 11 base pairs per turn.

17. The method of claim 1, wherein a polynucleotide scaffold:oligonucleotide helper/staple strand duplex is a nucleic acid homo or hetero-duplex assuming a helical twist characteristic of a chosen nucleic acid duplex.

18. The method of claim 1, wherein at least one crossover formed by the oligonucleotide helper/staple strand is antiparallel.

19. The method of claim 1, wherein helices comprise straight cylinders.

20. The method of claim 1, wherein crossovers are positioned to bend helices with a specified curvature.

21. The method of claim 1, wherein a region of the polynucleotide scaffold is left single-stranded without complementary staple strands.

22. The method of claim 21, wherein the single-stranded region allows mechanical flexibility between domains of the nanostructure.

23. The method of claim 21, wherein the single stranded region is designed to be bound by a plurality of extra oligonucleotides at some time after initial formation of the nanostructure that complement the single stranded region and change the shape of the nucleic acid nanostructure.

24. The method of claim 23, wherein the nanostructure is a cage for another type of molecule and a wall of the cage is actuated to open and close by the plurality of extra olignucleotides.

25. The method of claim 21, wherein the single stranded region allows capture of the nanostructure by an oligonucleotide probe complementary to the single-stranded region for purification of the nanostructure.

26. The method of claim 21, wherein the single stranded region is used in combination with helper strands elsewhere on the nanostructure to combine two or more nanostructures into a larger nanostructure.

27. The method of claim 1, wherein oligonucleotide helper/staple strands comprise single-stranded extensions for the capture of other single stranded oligonucleotides or agents bearing single-stranded oligonucleotides.

28. The method of claim 1, wherein a large stoichiometric excess of about 10 to 300 fold of oligonucleotide helper/staple strands is used to generate the nanostructure.

29. The method of claim 1, wherein the oligonucleotide helper/staple strands comprise sequences chosen to allow isothermal formation of the nanostructures without heat denaturation and annealing.

30. The method of claim 1, wherein the nanostructure comprises multiple nanostructures and each unit is combined to form nanostructures of larger finite or periodic nanostructures joined by stacking interactions between blunt-ended helices.

31. The method of claim 1, wherein the nanostructure comprises a plurality of nanostructures combined to form a larger finite or periodic nanostructure wherein each nanostructure comprises a single polynucleotide scaffold and wherein the scaffolds are joined by at least one specific helper/staple strand that bridges one nanostructures to another.

32. The method of claim 31, wherein the nanostructure comprises a cage for another molecule.

33. The method of claim 32, wherein the cage comprises oligonucleotides that actuate the opening and closing of the cage.

34. The method of claim 1, further comprising linking a desired composition to the nanostructure.

35. The method of claim 34, wherein the linking comprises using an interlacing agent.

36. The method of claim 34, wherein the composition comprises a nanoparticle.

37. The method of claim 36, wherein the nanostructure comprises a nano-circuit.

38. The method of claim 34, wherein the composition comprises a biological agent.

39. The method of claim 38, wherein the biological agent is a protein.

* * * * *